United States Patent [19]
Pometto, III et al.

[11] Patent Number: 5,595,893
[45] Date of Patent: Jan. 21, 1997

[54] IMMOBILIZATION OF MICROORGANISMS ON A SUPPORT MADE OF SYNTHETIC POLYMER AND PLANT MATERIAL

[75] Inventors: Anthony L. Pometto, III, Boone; Ali Demirci; Kenneth E. Johnson, both of Ames, all of Iowa

[73] Assignee: Iowa State University Research Foundation, Inc., Ames, Iowa

[21] Appl. No.: 254,476

[22] Filed: Jun. 6, 1994

Related U.S. Application Data

[63] Continuation of Ser. No. 901,528, Jun. 19, 1992, abandoned.

[51] Int. Cl.$^6$ ............................... C12P 7/40; C02F 3/00; C12N 11/12; C12N 11/08
[52] U.S. Cl. ............ 435/136; 210/615; 210/616; 435/147; 435/155; 435/160; 435/161; 435/175; 435/177; 435/178; 435/179; 435/180
[58] Field of Search ................. 435/174, 177, 435/178, 179, 180, 147, 155, 160, 161, 175; 210/615, 616

[56] References Cited

U.S. PATENT DOCUMENTS

| | | | |
|---|---|---|---|
| 3,275,580 | 9/1966 | Battista | 260/17.4 |
| 3,856,724 | 12/1974 | O'Connor | 260/17.4 |
| 4,506,012 | 3/1985 | Reed | 435/139 |
| 4,717,743 | 1/1988 | Wakabayashi | 524/13 |
| 4,814,273 | 3/1989 | Brumm | 435/140 |
| 4,833,181 | 5/1989 | Narukawa | 524/13 |
| 4,898,817 | 2/1990 | Yamazaki | 435/49 |
| 4,921,803 | 5/1990 | Nohr | 435/179 |
| 4,981,798 | 1/1991 | Kamakura | 435/179 |
| 5,145,779 | 9/1992 | Pometto, III et al. | 435/170 X |

OTHER PUBLICATIONS

Atkinson et al., *Trans. Instn. Chem. Engrs.* 50:208–216 (1972).
Atkinson et al., *Biotechnol. Bioeng.* 17:1245–1267 (1975).
Audet et al., *Appl. Microbiol Biotechnol.* 11:11–18 (1988).
Boyaval et al., *Enzyme Microb. Technol.* 10:725–728 (1988).
Bryers J. D., *Biotechnol. Bioeng.* 24:2451–2476 (1982).
Characklis, W. G., Biofilm development: A process Analysis, In Microbial Adhesion and Aggregation, ed. K. C. Marshall, pp. 137–157, Dahlem Konferenzen, New York (1984).
Characklis et al., *Biofilms*, pp. 671–696, John Willey and Sons, Inc., New York (1990).
Crueger et al., *A Textbook of Industrial Microbiology*, Chapt. 5 (pp. 64–110) and Chap. 17 (pp. 317–325), Sinauer Associates, Inc., Sunderland, MA (1989).
Demain et al., *Industrial Microbiology and biotechnology*, Chapters 18–26, American Society for Microbiology, Washington, D.C., 1986 (1989).
Friedman et al., *Biotech. Bioeng.* 12:961–974 (1980).
Ho, *Process Biochem.* 10:148–152 (1986).
Hongo et al., *Appl. Environ. Microbiol.* 52:314–319 (1986).
Kurt et al., *Biotech. Bioeng.* 29:493–501 (1987).
Lipinsky et al., *Chem. Eng. Prog.* (Aug.):26–32 (1986).
Ohleyer et al., *Appl. Biochem. Biotechnol.* 11:457–463 (1985).
Ohleyer et al., *Appl. Biochem. Biotechnol.* 11:317–331 (1986).
Pometto et al., *Appl. Environ. Microbiol.* 52:246–250 (1986).
Roy et al., *Biotechnol. Lett.* 8:483–488 (1982).
Scott, C. D., *Enzyme Microb. Tech.* 9:66–73 (1987).
Stenroos et al., *Biotechnol, Lett.* 4:159–164 (1982).
Telling et al., *Adv. Appl. Microbiol.* 13:91–116 (1970).
Vega et al., *Enzyme Microb. Technol.* 10:390–402 (1988).
ZoBell, C. E., *J. Bacteriol.* 46:39–43 (1943).
Evangelista, et al., *Ind. Eng. Chem. Res.*, vol. 30, No 8, 1991 (pp. 1841–1846).
Hawley, G. G., The Condensed Chemical Dictionary, Eighth edition, 1971, (pp. 753–930).

*Primary Examiner*—David M. Naff
*Attorney, Agent, or Firm*—Schwegman, Lundberg, Woessner & Kluth, P.A.

[57] ABSTRACT

A solid support for immobilization of microorganism cells is made of a synthetic polymer such as a polyolefin, in admixture with an organic polymeric plant material such as corn fibers, oat hulls, starch, and cellulose. Preferably, the synthetic polymer is in an amount of about 50–95% wt-% and the plant material is in an amount of about 5–50 wt-%. Preferred polyolefins are polyethylene and polypropylene. The plant material may be a mixture including a plant material that functions as a nutrient to enhance growth of the microorganism on the support. The support may be produced by combining the synthetic polymer and plant material to form a composite, dough-like thermoplastic composition. The composition may be prepared in an extrusion mixer and co-extruded as an extrudate to form a shaped article. The supports are useful for immobilizing living cells of a microorganism to form a biofilm reactor for use in continuous fermentations, in streams for bioremediation of contaminants, and in waste treatment systems to remove contaminants and reduce biochemical oxygen demand levels.

20 Claims, 4 Drawing Sheets

IMMOBILIZATION OF MICROORGANISMS ON A SUPPORT MADE OF SYNTHETIC POLYMER AND PLANT MATERIAL

This is a continuation of application Ser. No. 07/901,528, filed Jun. 19, 1992, now abandoned.

BACKGROUND OF THE INVENTION

Microorganisms are grown commercially in suspension cultures, and in solid-state and immobilized-cell fermentations. In immobilized-cell bioreactor systems, the substrate and microbial end-products are in a mobile liquid phase which is continually entering and exiting the reaction vessel. In this system, microbial cells are attached to or entrapped in an artifical or natural solid matrix, in an attempt to maintain a high population of slow or non-growing cells in the reaction medium. Some common matrix materials that are used for immobilizing microbial cells include calcium alginate and κ-carrageenan.

A drawback of such immobilized cell fermentation systems is diffusion of substrate into and product out of the matrix. In addition, interfering enzymes must either be eliminated from the system or inactivated. Also, the substrate and end-products in immobilized cell fermentations must be of a low molecular weight. Furthermore, release of microorganisms from the support matrix may occur in the late stages of fermentation which, in turn, decreases the life of the system.

In contrast to immobilized cell reactor systems that entrap microorganisms within a matrix, biofilm formation is a natural form of cell immobilization. A biofilm develops when microorganisms attach to an inert support that is made of a material such as stone, metal or wood. Filamentous microorganisms and actinomycetes will naturally stick to solid surfaces. There are also non-filamentous bacteria that will produce an extracellular polysaccharide that acts as a natural glue to immobilize the cells. In nature, nonfilament-forming microorganisms will stick to the biofilm surface, locating within an area of the biofilm that provides an optimal growth environment (i.e., pH, dissolved oxygen, nutrients). Since nutrients tend to concentrate on solid surfaces, a microorganism saves energy through cell adhesion to a solid surface rather than by growing unattached and obtaining nutrients randomly from the medium.

Biofilm formation has been used in various industrial applications, as for example, biological oxidation or reduction of industrial wastes, "quick" vinegar processes, animal tissue culture, and bacterial leaching of ores. Various attempts have been made to develop solid supports for immobilizing microorganisms to form biofilm reactors. For example, corn cob granules, polypropylene sheets, supports made of a cellulosic material (i.e., cellulose acetate, polyester cloth, cotton flannel, rayon, wood pulp, polyethylenimine-coated cotton), and a polymer-reinforced cotton gauze have been developed for use as cell immobilizing supports.

A disadvantage of current solid supports is that there is relatively low cell growth on the supports, and the cells of the microorganism tend to slough off from the surface of the support during the fermentation process. Also, supports made solely from agricultural plant materials tend to clump up in the aqueous medium. In addition, with the present supports, it is difficult to control the thickness of the immobilized cell layer.

Therefore, an object of the invention is to provide a composition for making a solid support with an increased capacity for immobilizing microbial cells, and which will facilitate cell growth in a continuous fermentation system and help prevent cell wash-out from a reaction vessel in a continuous fermentation system.

SUMMARY OF THE INVENTION

The present invention provides inert, solid supports that may be used for immobilizing cells of a microorganism to form a biofilm reactor. The supports are composed of a synthetic polymer, preferably a polyolefin such as polypropylene, in admixture with one or more plant-derived organic polymers such as corn fibers, oat hulls, cellulose, starch, and the like. The supports are substantially water-insoluble.

Preferably, the supports are composed of about 50–95 wt-% synthetic polymer, more preferably about 65–85 wt-%, and about 5–50 wt-% of at least one plant-derived organic polymer, more preferably about 20–30 wt-%. Optionally, but preferably, the plant-derived organic polymer is a mixture which includes a minor but effective amount of a plant-derived organic polymer that is selected to function as a microbial growth enhancing agent, as for example, a cellulose, a modified cellulose, a lignocellulose, a lignin, a protein such as zein, a starch, soy flour, and the like, alone or in combination, to provide added nutrients and to enhance the growth of the microorganism on the surface of the support.

The supports of the invention may be produced by combining a synthetic polymer and a plant-derived organic polymer in admixture to provide a composite, dough-like thermoplastic composition. The composition may be prepared, for example, in an extrusion mixer and co-extruded as an extrudate to form a shaped support, or the composition may be molded into a shaped article or support according to techniques known in the art, as for example, by compression molding, injection molding, and the like.

The invention is further directed to a biofilm reactor comprising the solid support in combination with living cells of a microorganism that are attached to the surface of the support, preferably as a film. The cells of the microorganism may be immobilized on the surface of the support by contacting the support with an effective amount of a live microbial cell culture, preferably in a liquid medium, for a time period effective for cells of the microorganism to attach to the surface of the support. Preferably, the support is held in contact with the cell culture for a time period effective for the microorganism to grow over the surface of the support and form a film over a substantial portion, preferably a major portion, of the support surface.

A single microorganism cell culture may be immobilized on the support to form a "pure culture" biofilm reactor. Alternatively, cells of a biofilm-forming microorganism such as Pseudomonas or Streptomyces, or a fungi such as Aspergillus, Penicillium or Saccharomyces, may be initially immobilized on the surface of the supports, and then a non- or low-film forming microorganism such as Lactobacillus, Zymgnonas or Clostridium may be immobilized on the cells of the film-forming microorganism attached to the surface of the support to form a "mixed culture" biofilm reactor.

According to the invention, the biofilm reactor (i.e., support with attached microbial cells) may be used in a variety of systems, as for example, in a continuous fermentation process to produce a fermentation product such as lactic acid, acetic acid, citric acid, succinic acid, propionic acid, and other like organic acids, or ethanol or butanol-acetone, or other like organic alcohols; in a chemically contaminated stream for bioremediation; in a waste treatment system to remove recalcitrant compounds and to reduce the biochemical oxygen demand; and the like. In such systems, the biofilm-covered support may be placed or positioned in a liquid medium that includes a substance, as for example, a carbohydrate or a contaminant substance such as petrochemicals, herbicides or pesticides, to be processed, i.e., metabolized, by the microorganism, and then the microorganism is allowed to substantially metabolize the substance to provide a microbial end-product.

The biofilm reactor of the present invention facilitates cell growth in a continuous fermentation system, and helps prevent cell wash-out from the reactor vessel, thus keeping cell density in the biofilm reactor at a high level. The supports of the present invention have an increased capacity to promote and maintain cell attachment and growth, and for adsorption and retention of the cells on the surface of the supports, than do supports that are made of a synthetic polymer such as a polyolefin, or of cellulose-based materials alone. Advantageously, the supports are lightweight and buoyant in an aqueous medium, and thus can be readily removed from the surface of a liquid medium. Moreover, the present synthetic polymer/plant-derived organic polymer composite supports reduce capital costs for construction of biofilm reactors, because of their light weight.

DETAILED DESCRIPTION OF THE INVENTION

Figure 1A:
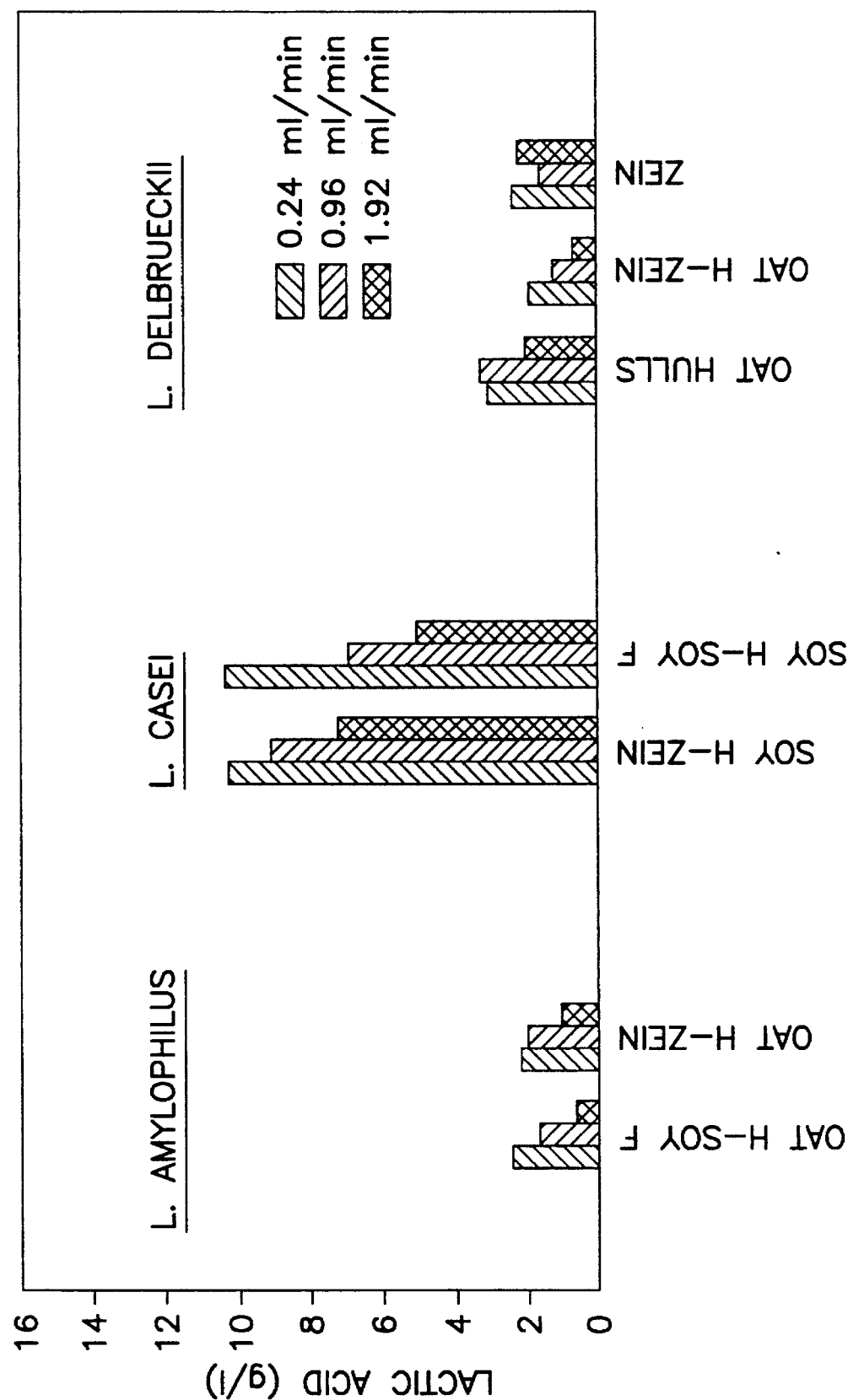
FIGS. 1A and 1B are is a graphical depiction of a continuous lactic acid production for pure cultures (FIG. 1A, lactic acid bacteria, alone) and mixed cultures (FIG. 1B, biofilm-forming bacteria and lactic acid bacteria) on selected supports.

The present invention provides a thermoplastic composition composed of, in admixture, a synthetic polymer and a plant-derived organic polymer, the plant-derived polymer optionally comprising a plant-derived growth enhancing agent. The composition is preferably shaped into a solid support that is useful for immobilizing cells of a microorganism, as for example, for use in a continuous fermentation process. The supports are substantially inert to the medium, substantially water-insoluble, and buoyant in an aqueous medium.

The combined amounts of the plant-derived organic polymer and the synthetic polymer in the present compositions are effective to provide a thermoplastic support having a level of structural stability and water resistance such that the support, when exposed to a liquid such as an aqueous culture medium, will remain essentially intact without significant deterioration for an extended period of time, preferably for about 1–3 years. Preferably, the composition comprises about 50–95 wt-% synthetic polymer, more preferably about 65–85 wt-%, even more preferably about 70–80 wt-%.

Suitable synthetic polymers that may be used in the present compositions include, but are not limited to, polyolefins, polycarbonates, polysulfones, and the like. Preferably, the synthetic polymer is a polyolefin. Polyolefins that are useful according to the invention include, for example, polyalkylenes such as polyethylene, polypropylene, polybutene, polyisoprene, polystyrene, polypentene, polymethylpentene, polybutadiene, polychloroprene, polyvinylchloride, polyvinylidene chloride, polyacrylonitrile, and the like, or a copolymer thereof, or a polyester, polyamide or polyimide such as polyvinylacetate, polyacrylamide, and the like, or a copolymer thereof.

As used herein, the term "plant-derived organic polymer" or polymer mixture includes a native or natural plant or plant part that substantially comprises a particular substance or combination of organic polymers, such as, but not limited to, polysaccharides such as cellulose, hemicellulose, lignocellulose, chitin, starch, xylan, inulin, and the like.

A plant-derived organic polymer or polymer mixture is included in the present thermoplastic compositions in an amount effective to provide a water-insoluble natural matrix of sufficient surface area within the inert polymer to provide a long-lasting rigid structure. Preferably, the composition is composed of about 5–50 wt-% of a plant-derived organic polymer, more preferably about 15–35 wt-%, even more preferably about 20–30 wt-%. A preferred plant-derived organic polymer is composed of from about 50–75 wt-% to about 80–95 wt-% lignocellulose.

Plant-derived organic polymers that are useful according to the invention include, but are not limited to, those provided in the form of a plant or plant part such as corn fibers, stovers, corn hulls, oat hulls, soy hulls, milkweed pods, leaves, seeds, fruit, grass, wood, paper, algae, cotton, hemp, flax, jute, ramie, kapok, a hard or soft wood, or any combination thereof. The plant-derived organic polymer may also be a flour or starch derived from, for example, but not limited to, corn, potatoes, wheat, rice, waxy maize, waxy rice, high amylose corn, tapioca, oats, rye, barley, sorghum, mung bean, sweet potatoes, or any combination thereof. Examples of plant-derived proteins useful as the plant-derived organic component of the present invention include, for example, gluten, zein, soybean protein, hordein, kafirin, avenin, xylan, and the like. It is also understood that the plant-derived organic polymer may be a separate component (i.e., cellulose, lignin, hemicellulose, protein, and the like) that has been extracted or otherwise separated from a plant or plant part, according to known techniques in the art.

Preferably, the plant-derived organic polymer is a native or natural fibrous plant material that is chemically unmodified. However, the plant-derived organic polymer may also be a component of the plant that has been chemically modified, as for example, a cellulosic substance (i.e., chemically modified cellulose) such as an ether derivative such as methylcellulose, carboxymethylcellulose or hydroxyalkyl cellulose; an ester derivative such as cellulose acetate; a nitrated cellulose such as nitrocellulose; and a xanthate derivative such as rayon or cellophane or viscose.

A preferred composition, prior to molding, contains about 50–95 wt-% synthetic polymer, more preferably about 65–85 wt-%, even more preferably about 70–80 wt-%, with polyolefins such as polypropylene and polyethylene being preferred; about 5–50 wt-% plant-derived organic polymer, more preferably about 15–35 wt-%, even more preferably about 20–30 wt-%, with corn fibers, oat hulls and soy hulls being preferred; and a moisture content of about 1.0 to 10 wt-%, more preferably about 0.1 to 2.0 wt-%.

The plant-derived organic polymer may optionally be a mixture of one or more organic polymers which includes a minor but effective amount of a plant-derived growth enhancing agent, to provide an additional nutrient source for the microorganisms to be immobilized onto the support, to enhance cell attachment and/or cell growth on the surface of the supports. Preferably, where included, the total amount of plant-derived organic polymer will include about 0.05 to 20 wt-% growth enhancing agent, more preferably about 0.1 to 5 wt-%. Preferably, the growth enhancing agent is added to the composition in the form of a plant or plant part, but may also be added as a substance that is isolated, separated or derived from a plant such as cellulose, starch, flour, and the like.

Suitable plant-derived growth enhancing agents include a cellulose substance derived from, for example, a textile fiber such as cotton, hemp, flax, jute, ramie, kapok, or a non-textile fiber such as a hard or soft wood; a cellulosic (i.e., chemically modified cellulose) substance, as described hereinabove; a lignocellulose derived from, as for example, corn fibers, oat hulls, soy hulls, wood, and the like; a starch such as corn starch, potato starch, wheat starch, rice starch, oat starch, and the like; or a plant-derived protein such as zein, gluten, soybean protein, and the like. The composition may further include a minor but effective amount of an animal-derived growth enhancing agent, as for example, an animal-derived protein such as casein derived from milk, albumin derived from blood or egg, collagen, gelatin, keratin, and other like protein-containing substances; or any combination thereof.

The compositions may further include a minor but effective amount of a compatible plasticizer to facilitate processing of the synthetic polymer/plant-derived polymer thermoplastic compositions to form the supports of the invention, and to increase the flexibility and toughness of the formed support. For example, suitable plasticizers according to the invention, include low molecular weight hydrophilic organic compounds such as dihydric or polyhydric alcohols and derivatives thereof, as for example, glycerol, glycerol monoacetate, diacetate or triacetate, sorbitol, sorbitan, mannitol, maltitol, ethylene glycol, diethyl glycol, propylene glycol, polyvinyl alcohol, and the like; sodium cellulose glycolate, cellose methyl ether, and the like; sodium diethysuccinate, triethyl citrate, and the like; and polyalkylene oxides such as polyethylene glycols, polypropylene glycols, polyethylene propylene glycols, polyethylene glycol fatty acid esters, and the like. The amount of plasticizer that would be included in the present compositions is about 0.2 to 10 wt-%, preferably about 0.5 to 5 wt-%.

The composition also contain a minor but effective amount of a lubricating agent effective to provide a mold- or dye-lubricating effect when the composition is molded into the desired article, for example, by aiding in the release of the molded article from the mold. Examples of suitable lubricants that may be used in the compositions, either alone or in combination with another lubricant, include mono- and diglycerides, and fatty acids, preferably saturated fatty acids; phospholipids such as lecithin; phosphoric acid-derivatives of the esters of polyhydroxy compounds; vegetable oil, preferably hydrogenated forms; animal fats, preferably hydrogenated forms to prevent thermal oxidation; and petroleum silicone and mineral oils. The amount of lubricant contained in the composition is preferably about 0.1 to 2 wt-%.

A compatible antimicrobial agent such as a fungicide or bactericide may also be included in the composition in an amount effective to prevent growth of an undesirable fungi, bacteria and the like, on the support. The antimicrobial agent should not inhibit the growth of the film-forming bacteria or the fermenting bacteria, nor should the agent induce undesirable interactions or chemical reactions between the components of the composition.

The present thermoplastic composition may be formed into a variety of articles having a desired shape, size and dimension, according to known processes in the art for molding thermoplastic materials. For example, the composition may be shaped by compression molding wherein direct pressure is applied using a hydraulic press on an amount of the composition contained in a cavity; by injection molding wherein an amount of the plastic composition in melted form is forced into a mold and maintained under pressure until cool; by blow molding wherein a tube of the thermoplastic composition is extruded into a mold and air pressure is applied to the inside of the tube to conform it to the mold and form a hollow article; and by other methods such as rotation molding, transfer molding, extrusion molding, vacuum forming, expanded foam molding, pressure forming, and inflation molding.

The solid supports may be contacted with living cells of a microorganism that then become attached to the surface of the support, preferably as a film, to form a biofilm reactor. As used herein, the term "biofilm reactor" is meant to include a support according to the invention, in combination with cells of a microorganism that are attached on the surface of the support, preferably in the form of a film or thin coating.

The cells of the microorganism may be immobilized on the surface of the support by contacting the support with a live microbial cell culture for a time period effective for cells of the microorganism to attach to the surface of the support. Preferably, the support is held in contact with the cell culture for a time period effective for the microorganism to grow over the surface of the support and form a coherent film over a substantial portion of the support surface.

A "pure culture" biofilm reactor may be formed by immobilizing a culture of single microbe onto the support. Alternatively, a "mixed culture" biofilm reactor may be prepared by first immobilizing cells of a biofilm-forming microorganism on the surface of the support, and then immobilizing a non- or low-film forming microorganism onto the cells of the biofilm-forming microorganism on the support.

Suitable microrganisms that may be used for attaching to and forming a film or coating layer on the surface of the supports include, for example, Pseudomonas spp. such as *Pseudomonas fragi, P. fluorescens, P. putide,* and others; Streptomyces spp. such as *Streptomyces viridosporus, S. badius, S. setonii,* and others; Thermoactinomyces spp. such as *Thermoactinomyces vulgaris* and others; bacteria such as cyanobacteria, methanogenic bacteria, chemolithotropic bacteria, and the like; or fungi, as for example, a Basidiomycetes, a Deuteromycetes, a Phycomycetes such as Rhizopus spp. and others, and a Ascomycetes such as Pencillium spp., Saccharomyces spp. and Aspergillus spp., as for example, *Aspergillus niger,* and others.

Non- or low-film forming microorganisms that are useful in the invention include, for example, Lactobacillus spp. such as *Lactobacillus casei, L. amylophilus, L. delbrueckii, L. pantarum,* and the like; Zymononas spp. such as *Zymononas mobilis,* and others; Clostridium spp. such as *Clostridium formicoaceticum, C. thermoautotrophicum, C. butyricum,* and others; Acetobacterium spp. such as *Acetobacterium woodii,* and others; Propionibacterium spp.i and Acetoqenium spp. such as *Acetogenium kivui,* and others.

The fermentations may utilize a microorganism that ferments a carbohydrate to a single organic acid as the principal end-product, as for example, *Lactobacillus casei* (lactic acid), *Lactobacillus delbrueckii* (lactic acid), *Clostridium*

*formicoaceticum* (acetic acid), *Clostridium thermoautotrophicum* (acetic acid), *Acetobacterium woodii* (acetic acid), *Acetogenium kivui* (acetic acid), *Aspergillis niger* (citric acid), and the like. An organic alcohol may also be produced as the end product, via fermentations with, for example, *Zymononas mobilis* (ethanol) or *Clostridium butyricum* (butanol-acetone).

In a fermentation process, such as a continuous or batch fermentation, it is preferred that the pH, temperature and dilution rate are effective to produce the fermentation product, as for example, an organic acid or alcohol, at an amount of about 5 to 90 g/l per hour, more preferably about 15–60 g/l per hour. Preferably the pH is about 4 to about 7.5, more preferably about pH 5 to 6; the temperature is about 25° C. to about 70° C., more preferably about 25° C. to about 45° C.; and the dilution rate is about 0.4 to about 7.5 per hour, more preferably about 0.6 to about 5 per hour.

In a system for treating water (i.e., stream or waste treatment system), it is preferred that the microbial consortium on the biofilm reactor be enriched to degrade the chemical contaminants in the water to substantially reduce the biochemical oxygen demand (BOD) in the water. The biofilm reactor may optionally be combined within a containing structure that is capable of floating at the surface of the water, as for example, a floating aeration system, and the contaminated water may be sprayed over the biofilm reactor to accelerate biodegradation.

It was found that microbial affinity for the supports will vary according to the particular ingredients used in the formulation of the composition and support. Accordingly, it is preferred that an initial screening be performed to determine a match between the support and the microorganisms to be immobilized, that will optimize attachment of the microorganism on the surface of the support, and the growth of the organism to establish a biofilm layer.

The invention will be further described by reference to the following detailed examples. These examples are not meant to limit the scope of the invention that has been set forth in the foregoing description. It should be understood that many variations and modifications may be made while remaining within the spirit and scope of the invention. The disclosures of the cited references are incorporated by reference herein.

EXAMPLE 1

PREPARATION OF POLYOLEFIN COMPOSITE SUPPORTS

In the following example, different polyolefin composite supports were prepared. Polyolefin (i.e., polypropylene) (pp-composite) composite chips containing 25% (w/w) plant-derived organic polymer were used as solid supports (see, TABLE 1). The pp-composite chips were prepared by using high temperature extrusion with a Brabender PL2000 twin-screw extruder (C. W. Brabender Instruments, Inc., South Hackensack, N.J.) with barrel temperatures of 200° C., 210° C., and 220° C., a die temperature of 220° C., and a screw speed of 20 rpm. Polypropylene was donated by Quantum USI Division (Rolling Meadows, Ill.). Plant-derived organic polymers used were cellulose (Sigma Chemical Co., St. Louis, Mo.), corn fiber (Penford Products Co., Cedar Rapids, Iowa), corn starch (American Amize-Products Co., Chicago, Ill.), oat hulls (National Oats Co., Cedar Rapids, Iowa), soybean flour (Archer Daniels Midland Company, Decatur, Ill.), soy hulls (ISU Center for Crops Utilization Research, Ames, Iowa), and zein (Sigma Chemical Co.). In this example, supports in the form of chips were produced from extruded rods. It is understood, however, that the composition may be shaped as desired.

The polyolefin/natural plant-derived organic polymer thermoplastic composition may be formed into a solid support having virtually any shape or size to accomodate a particular application.

EXAMPLE 2

BIOFILM FORMATION ON VARIOUS INERT SUPPORTS

Microbial attachment to an inert support, or "biofilm formation," is a natural mechanism for cell immobilization. In the following example, a total of 12 species of biofilm-forming bacteria selected from the genuses Bacillus, Pseudomonas, Streptomyces, and Thermoactinomyces, were evaluated for attachment after either batch or continuous fermentation, to supports composed of pea gravel, porcelain berl saddles, 3M-macrolite ceramic spheres and twelve combinations of polypropylene composite (pp-composite) chips with various plant-derived organic polymers. The results indicate that the best biofilm-forming bacteria were *Pseudomonas fragi* (ATCC 4973), *Streptomyces viridosporus* T7A (ATCC 39115), and *Thermoactinomyces vulgaris* (NRRL B-5790) which grow at room temperature (25° C.), 37° C., and 45° C., respectively.

For pure culture and mixed culture continuous lactic acid fermentation, the lactic acid bacteria used were *Lactobacillus amylophilus* (NRRL B-4437), *Lactobacillus casei* (ATCC 11443), and *Lactobacillus delbrueckii* mutant DP3. The biofilm formed on each support was evaluated according to clumping properties, weight gain and Gram staining after drying at 70° C. overnight (15 hours).

For mixed culture fermentations, inert supports were dry heat sterilized, followed by at least 15 days of continuous fermentation with the biofilm-forming bacteria. The culture medium was then changed to heat sterilized MRS Lactobacillus broth, and each biofilm reactor was aseptically inoculated with a species of lactic acid bacteria.

For evaluation of each of the inert supports and the control under pure culture conditions, the lactic acid bacteria only was inoculated into the reactor vessel containing a sterile, uninoculated support, or into a reactor vessel containing no chips ("control"). Continuous fermentation was started and each of the different flow rates ranging from 0.06 to 1.92 ml/minute, was held constant for 24 hours. Lactic acid production was determined by high performance liquid chromatography (HPLC). The results show that *Streptomyces viridosporus* and *Lactobacillus casei* in combination with the pp-composite chips showed the best biofilm formation.

MATERIALS AND METHODS

Microorganisms. Bacteria evaluated for biofilm formation were obtained from either American Type Culture Collection (ATCC) (Rockville, Md.) or Northern Regional Research Laboratory (NRRL) (Peoria, Ill.) (see TABLE 2).

Solid supports. The supports evaluated were pea gravels obtained from a municipal park, porcelain berl saddles (Aldrich Chemical Company, Milwaukee, Wis.), 3M-macrolite ceramic spheres (Aluminum oxide) (Industrial Mineral Product Products Division/3M, St. Paul, Minn.), bentonite and kaolite (ISU Agronomy Department), and polypropylene (pp) composite chips containing 25% (w/w)

of a plant-derived organic polymer. Porcelain berl saddles were pretreated to stimulate biofilm development. Saddle pretreatments included (a) autoclaving the saddles in various complex medium (i.e. Lactobacillus MRS broth, trypticase soy broth, soluble starch broth, yeast extract medium, a nutrient broth) to increase the concentration of nutrients on the surface of the saddles, or (b) treatment of the saddles with an acid or a base (2N $H_2SO_4$, 2N HCl, or 2N NaOH) for 48 hours at room temperature (25° C.).

Polypropylene composite chips (pp-composite) were prepared as described hereinabove in Example 1. Plant-derived organic polymers used were carboxyl methyl cellulose (Sigma Chemical Co., St Louis, Mo.), cellulose (Sigma Chemical Co., St. Louis, Mo.), ground (20 mesh) oat hulls (National Oat, Cedar Rapids, Iowa), soy hulls (Center for Crops Utilization Research at ISU, Ames, Iowa), soy flour, zein (Sigma Chemical Co., St. Louis, Mo.), and xylan. Each of the plant-derived organic polymers was vacuum dried for 48 hours. Polypropylene composite chips (pp-composite chips) were compounded into solid supports by combining polypropylene with different levels and blends of plant-derived organic polymers (see TABLE 3).

Biofilm evaluations. Biofilm formed on the solid supports was evaluated gravimetrically (weight gain or loss), by clumping characteristics after drying the supports at 70° C. overnight (15 hours), and by Gram staining the pp-composite chips at the end of a batch or continuous fermentation. For Gram staining, a portion of pp-composite chips, obtained from time zero ($T_0$) and at the end of fermentation, were separately placed in test tubes, and Gram staining was performed in the individual test tubes. The chips were washed with alcohol until all excess color was eliminated. The chips were then dried at 70° C. overnight (15 hours). All biofilm evaluations were compared to uninoculated supports ("controls").

Biofilm formation in batch fermentation systems. The different solid supports were weighed and placed in 30-ml culture tubes, 10 ml of a specific culture medium was added to each of the tubes, and the supports and medium were sterilized at 121° C. and 15 psi for 15 minutes. Each support was inoculated from a specific culture slant, fitted with a bubbler tube unit (A. L. Pometto, III, et al., *Appl. Envir. Microbiol.* 52:246–250 (1986)), then incubated at the temperature corresponding to the optimum temperature for the particular inoculant, under continuous aeration with $CO_2$-free air. The control tubes were prepared and treated the same, but were not inoculated with a microbial culture. After a 5–7 day incubation, the culture medium was drained from the culture tubes, the solid supports were rinsed with deionized water, placed into a preweighed 250-ml flask and dried at 70° C. overnight (15 hours). After equilibration, the flasks were reweighed. Before and after drying, each support was visually evaluated for clumping and for cell mass accumulation.

Biofilm formation in continuous fermentation systems. Each solid support was weighed, placed in a 50-ml plastic syringe fitted with a silicone stopper, and connected at the hypodermic end to a 10-liter carboy containing 4 liters of a corresponding growth medium, and to a separate airline with a filter. The supports and medium were autoclaved at 121° C. for 1 hour. After cooling, the 50-ml syringe reactor vessels were placed into water baths at a growth temperature corresponding to the optimal temperature for the bacterial inoculant, medium was pumped into the reactor vessel to fill it, and then the medium was inoculated from a fresh bacterial culture. Each reactor vessel was incubated as a batch culture for 24 hours with continuous aeration. Culture medium was then continuously pumped into the fixed volume reactor vessel at a rate of 0.06 ml/minute for 6 weeks. The solid supports were then evaluated for biofilm formation by draining off the culture medium, rinsing the supports with deionized water, placing the supports into a preweighed flask, drying at 70° C. for 24 hours, and equilibrating the support in a desiccator. The supports were evaluated for clumping properties, weight change and Gram staining (pp-composite chips only).

Continuous and batch lactic acid fermentation. The results showed that the best biofilm-forming bacteria were *Pseudomonas fragi* (ATCC 4973), *Streptomyces viridosporus* T7A (ATCC 39115), and *Thermoactinomyces vulgaris* (NRRL B-5790) which grow at room temperature (25° C.), 37° C., and 45° C., respectively. For pure culture and mixed culture continuous lactic acid fermentation, the lactic acid bacteria used were *Lactobacillus amylophilus* (NRRL B-4437), *Lactobacillus casei* (ATCC 11443), and *Lactobacillus delbrueckii* mutant DP3, in combination, respectively, with *P. fragi*, *S. viridosporus* and *T. vulgaris*. The biofilm-forming bacteria and lactic acid bacteria pairs had corresponding temperature optimums.

For mixed culture fermentations, the different inert supports were heat sterilized (dry) followed by at least 15 days continuous fermentation with a biofilm-forming bacteria (see TABLE 4). The culture medium was then changed to heat-sterilized MRS Lactobacillus broth, and each reactor vessel was aseptically inoculated with the corresponding lactic acid bacteria.

For pure culture evaluations of each of the different inert supports and the control, lactic acid bacteria was inoculated into reactor vessels containing sterile fresh supports, or a reactor vessel containing no chips (control). Continuous fermentation was commenced, and each different flow rate (0.06, 0.12, 0.24, 0.48, 0.96, 1.92 ml/minute) was held constant for 24 hours, with a sample taken every 4 or 5 hours. During continuous lactic acid fermentation, the pH, optical density (620 nm), % lactic acid, and % glucose in the effluent were analyzed, respectively, by using a pH-meter, a Bausch & Lomb Spectronic 20 spectrophotometer (Milton Roy, Mass.), and a Waters High Performance Liquid Chromatograph (HPLC) (Milford, Mass.), equipped with a Waters Model 401 refractive index detector. The HPLC separation of lactic acid, glucose, and other broth constituents was achieved on a Bio-Rad Aminex HPX-87H column (300×7.8 mm) (Bio-Rad Chemical Division, Richmond, Calif.) using 0.012 N $H_2SO_4$ as a mobile phase at a flow rate of 0.8 ml/minute with a 20-µl injection loop.

RESULTS AND DISCUSSION

Porcelain berl saddle in batch fermentations. For untreated saddles, no biofilm formation was observed for any of the bacteria (see TABLE 5). Therefore, different pretreatments were applied to these supports to stimulate biofilm formation. The saddles were autoclaved with different complex medium to increase the level of nutrients adhering to surface. The percent weight gain was proportional to the soluble solid concentration in the medium (see TABLE 6). A high soluble solid concentration increased the adhesiveness of the solid supports. Saddles were also subjected to 48-hour pretreatment in 2N $H_2SO_4$, HCL, or NaOH, washed in water, and then autoclaved in a different medium (see TABLE 7). Compared to the water control, a slight increase in soluble solid binding was observed for the 2N HCl treated saddles only. Biofilm formation was not effected by this pretreatment. Calcium addition had no effect on biofilm formation.

Pea gravel and 3M-macrolite spheres in batch fermentations. Both pea gravel supports and macrolite sphere supports showed some select biofilm formation (see TABLE 5). *Pseudomonas fragi* and *Pseudomonas amyloderamosa* formed a film, respectively, on pea stone and macrolite spheres. Films were formed on pea stone by three filamentous bacteria, and on macrolite spheres by six filamentous bacteria. It is noted, however, that pea stones are a mixture of different stone types and sizes, which makes the use of pea stones in fermentation systems unpredictable. The 3M-macrolite spheres were also unpredictable, since no weight gain was detected, only clumping of cells. Furthermore, floating spheres caused plugging in the system, which caused problems in the continuous fermentations.

Bentonite and kaolite in batch fermentations. The bentonite and kaolite had a weight difference exceeding 20%, which was likely due to hydration and dehydration of the materials.

EXAMPLE 3

MATCHING OF MICROORGANISMS WITH A SUPPORT

It was found that the microbial affinity for a particular support may vary according to a particular blend of the synthetic polymer and plant-derived organic polymer used to form the support. Therefore, it is preferred that there be an initial screening to match a support to a specific film-forming and/or low- or non-film-forming microorganism to provide optimal attachment of the microorganism to the support material.

Polypropylene composite chips in continuous fermentations. For all the pp-composite chips evaluated for biofilm formation with *Streptomyces viridosporus* T7A, *Thermoactinomyces vulgaris*, and *Pseudomonas fragi*, some weight loss was detected for each support. However, various clumping levels were observed during the fermentation and after the chips were harvested, washed, and dried (see, TABLE 8). For the pp-composite chips, some weight loss would be expected because of biodegradation or leaching of the plant-derived organic polymers from the chips. Furthermore, various levels of clumping were observed with different chip supports. Gram staining of the chips also confirmed the biofilm formation by observing significant color difference between time zero ($T_0$) chips and those tested after cultural incubation.

Optimization of biofilm formation on select supports. The results indicate that the best biofilm formers were *Pseudomonas fragi*, *Streptomyces viridosporus* T7A, and *Thermoactinomyces vulgaris* on pp-composite chips (see, TABLE 4). Each of these biofilm-forming bacteria grow at room temperature (25° C.), 37° C., and 45° C., respectively, permitting evaluation of different strains of lactic acid bacteria for mixed culture lactic acid fermentation. The time required for biofilm formation on the different pp-composite chips was determined by harvesting after 4, 8, and 15 days of continuous fermentations (see, TABLE 4). Results illustrated that good biofilms were formed for each bacterium after 15 days of incubation.

Mixed culture lactic acid fermentations. Lactic acid fermentations were performed at three different temperatures, room temperature (25° C.), 37° C., and 45° C. For each of the biofilm reactors containing selected pp-composite chips (see TABLE 4), pure (lactic acid bacteria, alone) and mixed (biofilm-forming bacteria and lactic acid bacteria) fermentations were evaluated.

Figure 1B:
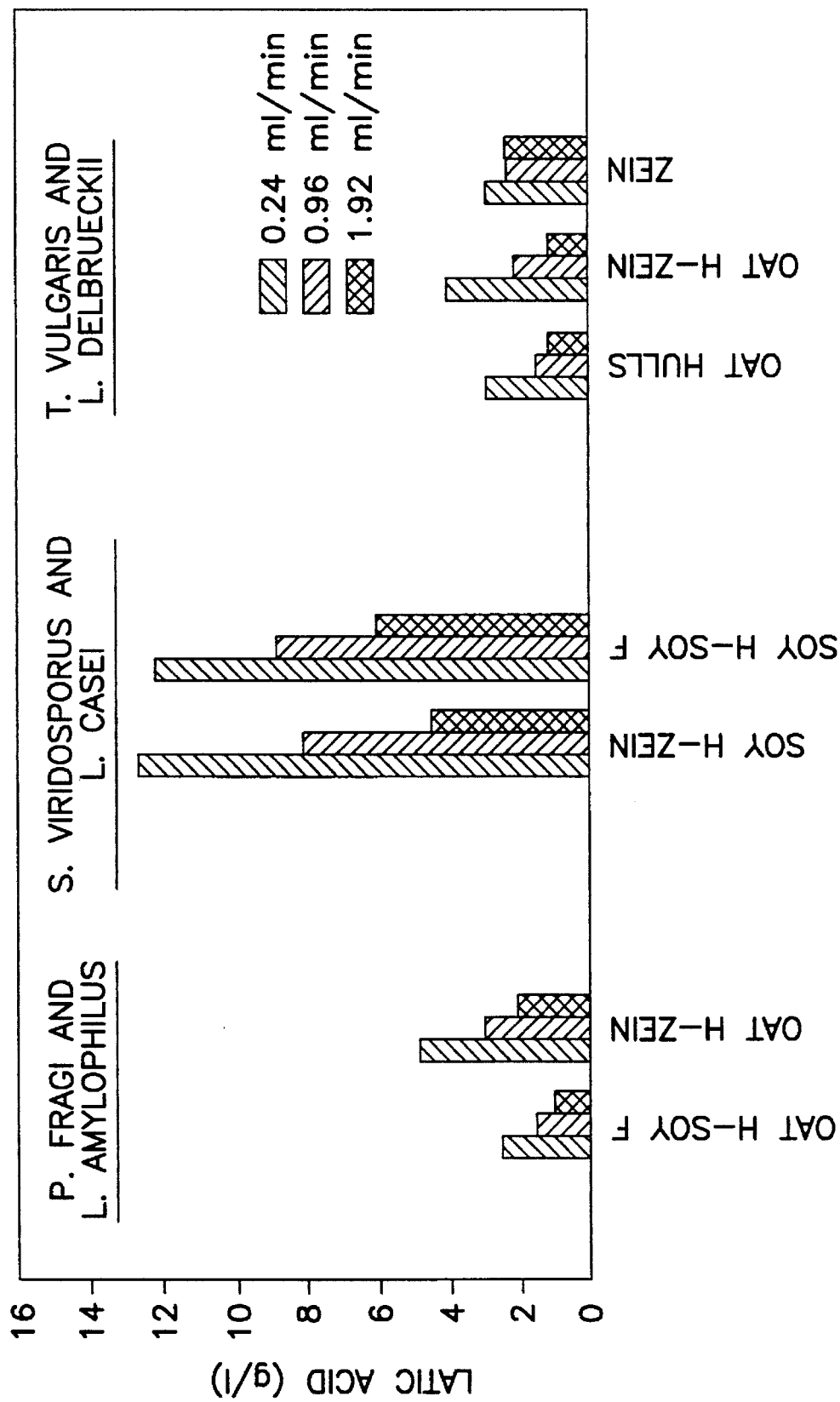

(a) *P. fragi* and *L. acidophilus* (room temperature). The pure culture (*L. acidophilus*, alone) and mixed culture continuous fermentations demonstrated a preference for two distinct pp-composite chips for biofilm fermentation, oat hull/soy flour and oat hull/zein polypropylene composite supports, respectively (see TABLE 9). For these preferred supports, the best lactic acid production was observed for 0.06 to 0.48 ml/minute flow rates, which produced a range of 2.28 to 3.97 g/l lactic acid for pure culture, and 2.92 to 4.82 g/l lactic acid for mixed culture fermentation. Maximum lactic acid production was observed for flow rates of 0.48 and 0.24 ml/minute for pure culture and mixed culture, respectively, with relatively stable lactic acid production occurring over a broader dilution rate for the mixed culture as compared to the pure culture (see, FIGS. 1A and 1B). However, at the highest lactic acid production levels, the percent yields were consistently lower for the mixed culture than the pure culture fermentations. For example, at the same flow rate of 0.48 ml/minute, lactic acid production was about the same for pure culture and for mixed culture fermentations (3.97 g/l and 3.59 g/l, respectively), whereas the percent yields were significantly different between the pure culture fermentations at 100% and the mixed culture fermentations at 81%. Approximately twice the level of cell mass in the fermentation effluent was observed in both the pure culture and the mixed culture continuous fermentations, with supports having the best lactic acid production (see, TABLE 9 and FIGS. 1A and 1B).

(b) *S. viridosporus* T7A and *L. casei* (37° C.). Both the soy hulls/zein and the soy hulls/soy flour pp-composite chips produced consistently high levels of lactic acid in pure culture (*L. casei* alone) and in mixed culture fermentations (see, TABLE 10). At nearly every flow rate, lactic acid production in the mixed culture fermentation was higher than in the pure culture fermentation. The higher performance for the mixed culture fermentations is likely the result of the higher level of Lactobacillus immobilization. For these supports, yields were high for both pure culture and mixed culture fermentations, with 100% yields produced at the faster flow rates. Both the pure culture and mixed culture fermentations produced a relatively constant level of lactic acid, up to 0.48 ml/minute, with a more gradual reduction being observed for the mixed culture fermentations (see, FIGS. 1A and 1B).

(c) *T. vulgaris* and *L. delbrueckii* DP3 (45° C.). The pure culture (*L. delbrueckii* alone) and the mixed culture fermentations demonstrated a preference for pp-composite supports containing oat hulls and zein, respectively (see, TABLE 11). However, the results show relatively consistent levels of lactic acid production for the mixed culture fermentations with all three pp-composite supports. Percent yields were consistently lower for the mixed culture fermentations. Furthermore, cell mass production in the effluent was highest for the pure culture on oat hull pp-composite supports, and generally at about the same level for all three supports for the mixed culture fermentations. Lactic acid production by the pure culture on oat hulls pp-composite chips and by the mixed culture on zein pp-composite chips is distinctly different, with a clear plateau for flow rate 0.24 to 0.96 and two distinct plateaus at 0.12 to 0.24 and 0.48 to 1.92, respectively (see, FIGS. 1A and 1B). Yields with the three supports were distinctly different with pure culture fermentations, with the best yields being with zein pp-composite supports, and consistently higher lactic acid production on the oat hull pp-composite supports, whereas the mixed culture fermentations had relatively consistent yields on all three supports.

Discussion. The lower levels of lactic acid production by *L. acidophilus* and *L. delbrueckii* DP3 were most likely due to sensitivity to reduced pH. Neither bacteria will grow a pH below 6, whereas *L casei*, which produced the highest level of lactic acid, is less sensitive (grows at pH >4.5). Therefore, with a pH-controlled bioreactor, *L. acidophilus* and *L. delbrueckii* would produce a higher level of lactic acid. However, both *L. acidophilus* and *L. delbrueckii* produced significantly higher levels of lactic acid in mixed culture fermentation than in pure culture (see, TABLES 9 and 11). These results indicate that mixed culture biofilms provide pH protection and/or stabilization for these fastidious bacteria.

Gram staining and clumping of cells on the inert supports were used to measure biofilm formation. The pp-composite chips produced the best biofilm formation. Continuous lactic acid fermentation may be enhanced by using biofilm fermentors containing specific polypropylene composite chips.

EXAMPLE 4

LACTIC ACID FERMENTATION USING MIXED CULTURE BIOFILM REACTOR

In the following example, the combination of the biofilm-forming bacteria, *Streptomyces viridosporus* T7A (ATCC 39115), and the lactic acid bacteria, *Lactobacillus casei* (ATCC 11443), was examined. A total of 16 different polypropylene composite (pp-composite) chips containing various kinds of plant-derived organic polymers were evaluated in 50-ml reactors with pure culture and mixed culture continuous lactic acid fermentations.

For mixed culture fermentations, a 15-day continuous fermentation with *S. viridosporus* in 0.6% yeast extract medium was performed initially to establish a biofilm on the chips. The culture medium was then changed to a heat sterilized MRS Lactobacillus broth and inoculated with *L. casei*. For pure culture evaluations of the different pp-composite chips, *L. casei* was inoculated directly into the reactors containing sterile pp-composite chips. Controls were composed of polypropylene-alone chips or a reactor containing no chips. Continuous fermentation was started and each flow rate (0.06, 0.12, 0.24, 0.48, 0.96, and 1.92 ml/minute) was held constant for 24 hours. Lactic acid production was determined throughout the 24 hours by high performance liquid chromatography (HPLC).

Lactic acid concentrations and production rates were consistently higher in mixed culture than in pure culture fermentations, with and without pp-composite chips. Production rates that were two to five times faster than the control with no chips were observed for the pure culture and mixed culture bioreactors. The results show higher cell retention and/or immobilization in the bioreactors due to *L. casei* interaction with the support and/or, in the case of mixed culture fermentations, with the biofilm former which developed differently for each support.

MATERIALS AND METHODS

Microorganisms and medium. *Streptomyces viridosporus* T7A (ATCC 39115) and *Lactobacillus casei* (ATCC 11443) were obtained from American Type Culture Collection (ATCC) (Rockville, Md.). For continuous fermentations, a 0.6% yeast extract medium (Difco Laboratories, Detroit, Mich.) (pH 7) in deionized water and a Lactobacillus MRS Broth (Difco) was used for *Streptomyces viridosporus* T7A and *Lactobacillus casei*, respectively.

Solid supports. Polypropylene (pp) composite chips containing 25% (w/w) plant-derived organic polymer were prepared as described hereinabove in Example 1.

Biofilm evaluations. Biofilm that formed on the solid supports was evaluated gravimetrically (weight gain or loss) by clumping characteristics after drying the supports at 70° C. overnight (15 hours), and by Gram staining of the chips at the end of the continuous fermentations. All biofilm evaluations were compared to uninoculated supports (controls).

Continuous lactic acid fermentation. Pure culture and mixed culture fermentations were evaluated in 50-ml bioreactors continuous fermentations with an approximate 25-ml working volume. Solid supports were weighed, placed in a 50-ml plastic syringe fitted with a silicone stopper, connected at the hypodermic end to a 10-liter carboy containing 4 liters of corresponding medium and a separate airline with filter. The complete system, including medium (4 liters), was autoclaved for 60 minutes at 121° C.

For mixed culture fermentations, supports were heat sterilized (dry), 0.6% yeast extract medium was added, and then a 0.1 ml spore suspension of *S. viridosporus* was added, followed by at least 15 days continuous fermentation at 37° C. for biofilm formation. Culture medium was then changed to heat sterilized MRS Lactobacillus broth, and each reactor was aseptically inoculated (0.1 ml) from a fresh culture of *L. casei* and incubated as a batch culture for 24 hours at 37° C. prior to continuous fermentation.

For pure culture evaluations of each different support and the control, lactic acid bacteria was inoculated into each reactor containing a sterile fresh support, or a reactor containing no chips ("control"). Continuous fermentation was commenced, and each different flow rate (0.06, 0.12, 0.24, 0.48, 0.96, 1.92 ml/minute) was held constant for 24 hours. The effluent was analyzed every 4 to 5 hours for changes in pH, absorbance (620 nm) on a Bausch & Lomb Spectronic 20 spectrophotometer (Milton Roy, Mass.), and lactic acid production and glucose consumption on a Waters High Performance Liquid Chromatograph (Milford, Mass.) equipped with Waters Model 401 refractive index detector. The separation of lactic acid, glucose, and other broth constituents was achieved on a Bio-Rad Aminex HPX-87H column (300×7.8 mm) (Bio-Rad Chemical Division, Richmond, Calif.) using 0.012 N $H_2SO_4$ as a mobile phase at a flow rate of 0.8 ml/minute with a 20-μl injection loop, and a column temperature of 65° C.

RESULTS AND DISCUSSION

Percent yield. The percent yield is a measure of the efficiency of bioconversion of glucose to lactic acid (see, TABLES 12-*a,b,c* and 13-*a,b*). In batch fermentations in stirred-tank reactors with the pH controlled to 5.0, *L. casei* had a yield of 90.8% for 138 hours of fermentation. In the present 25-ml continuous fermentations, percent yield ranged from 45% (corn fiber pp-composite supports; mixed culture) to 100%. For pure culture fermentations, a continuous increase in percent yield paralleled an increase in flow rate for the majority of pp-composite supports, including the controls. For mixed culture fermentations, however, in general, percent yield patterns were irregular, with the higher values correlating with the faster flow rates. The results indicate that biofilm former, *S. viridosporus* T7A, used some of the glucose at the early and slower flow rates of fermentation, and then this consumption decreased at the latter and faster flow rates, which also produced the higher yields.

Productivity rates. The productivity rate is a measure of lactic acid production per hour at the different flow rates (see, TABLES 12-a,b,c). With each doubling of flow rates, lactic acid production increased 1.58 to 1.88 times for pure culture, and 1.77 to 2.05 times for mixed culture, for each of the pp-composite supports, whereas in the controls, the cell suspension culture, and polypropylene alone support (pure culture) increased by 1.5 to 1.7 times (see, TABLE 13-a,b). Furthermore, productivity rates for several pure culture and mixed culture fermentations on pp-composite supports were 2 to 3 times higher when compared to the control at the same flow rates (see, TABLE 13-a,b, bold type values). The slower flow rates (0.06 and 0.12 ml/minute) showed productivity rates that were close to the suspension culture control, whereas the faster flow rates (0.24 to 1.92 ml/minute) generally showed significantly higher productivity rates for both the pure culture and mixed culture fermentations.

Lactic acid production. Lactic acid levels were consistently higher for each pp-composite support for pure- and mixed culture fermentations compared to both controls (cell suspension culture; polypropylene-alone), particularly at the three fastest flow rates (i.e., 0.48, 0.96 and 1.92 ml/minute) (see, FIGS. 2A and 2B). Furthermore, the mixed culture fermentation, in the majority of supports, produced a substantially higher level of product compared to the corresponding pure culture fermentation. These data illustrate the benefits of the mixed culture biofilm reactor for enhanced lactic acid production. Moreover, the higher cell density on each of the different supports by pure culture and mixed culture fermentation resulted in a net increase in lactic acid production.

Cell immobilization. Higher production rates in immobilized cell cultures is the result of higher cell density in the bioreactor, as determined by clumping and by Gram-staining of each chip at harvest. Compared to the pp-composite starting materials, Gram staining of each chip following incubation demonstrated an increased Gram positive appearance. These data and the significant increase in lactic acid production compared to the suspension culture control, indicate that higher cell densities occurred with each of the pp-composite support bioreactors.

Figure 2A:
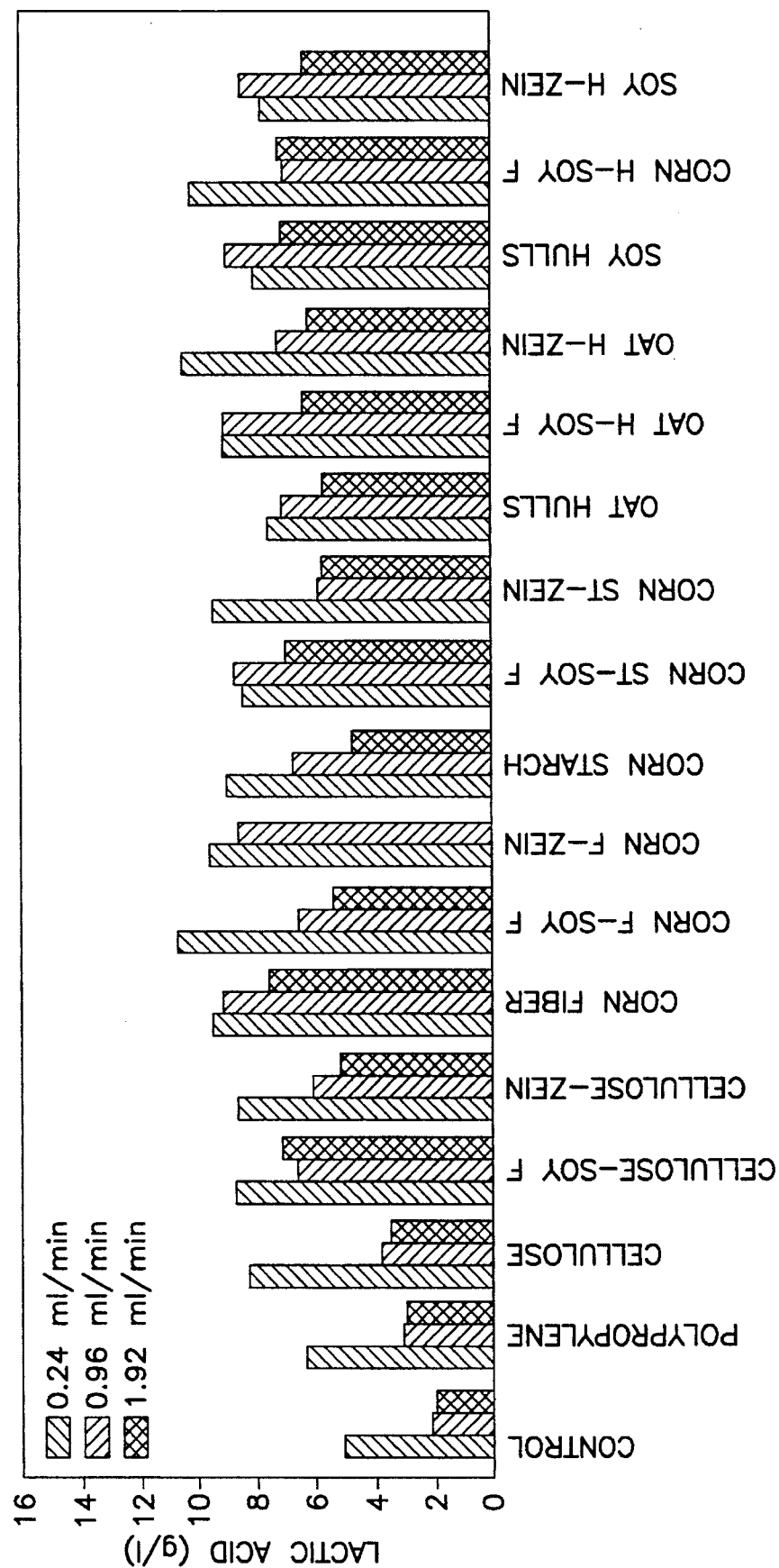
FIGS. 2A and 2B are is a graphical depiction of a continuous lactic acid production for pure (FIG. 2A) and mixed (FIG. 2B) cultures on 16 synthetic polymer/plant-derived organic polymer composite supports at higher flow rates.
Figure 2B:
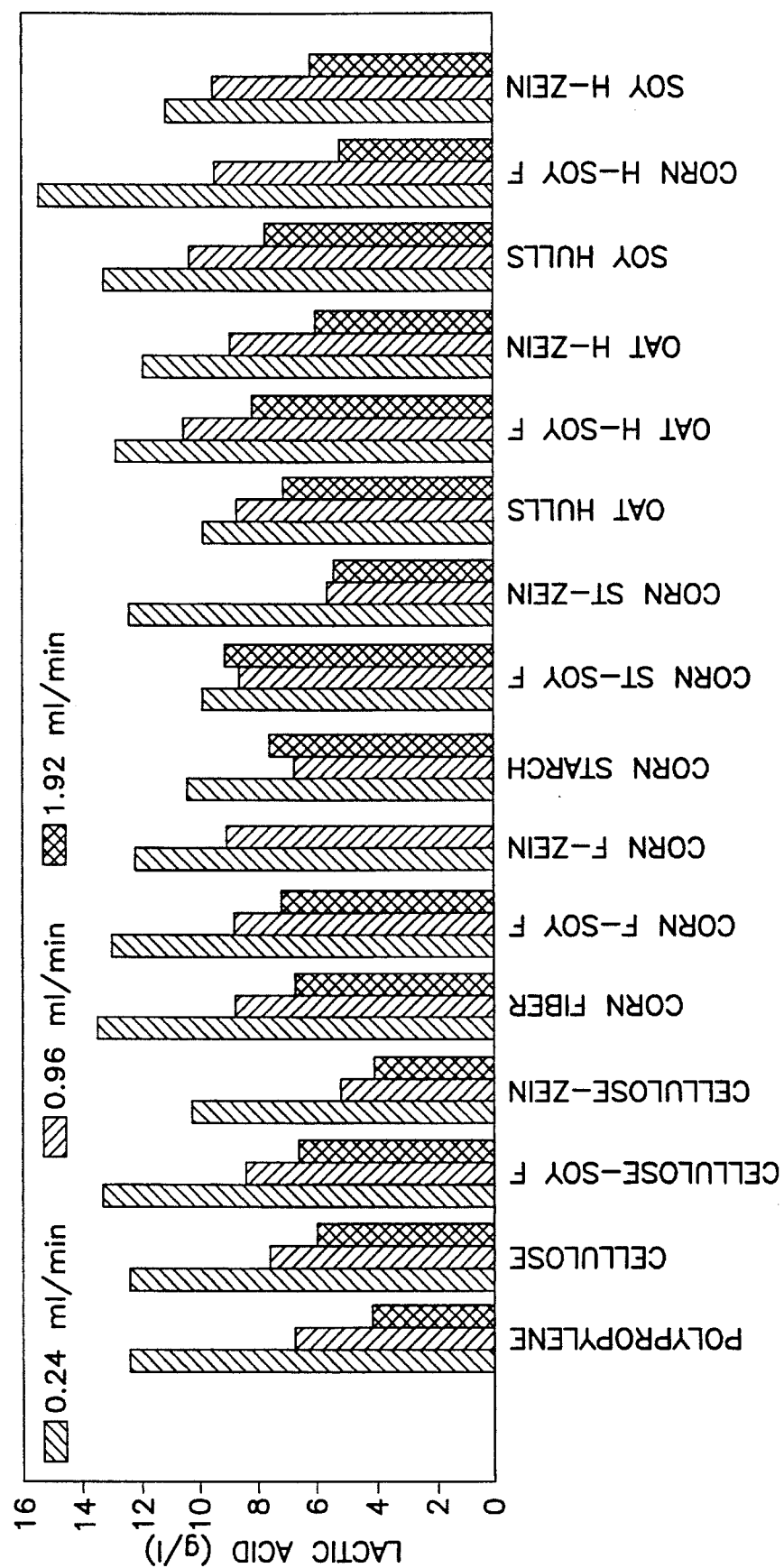

In addition, the benefit of a mixed culture fermentation in cell immobilization is illustrated by comparing pure culture and mixed culture fermentation on polypropylene-alone chips (see, FIGS. 2A and 2B). The data indicates that biofilm-forming Streptomyces acted as a natural immobilizer of the Lactobacillus onto the supports. Pure culture interaction with the different plant-derived organic polymers in the pp-composite supports had generally low values for the cellulose, corn starch, and oat hull pp-composite chips, and high values for corn fiber and soy hull pp-composite chips (see, TABLES 8 and 13-a,b). The data also shows that the addition of soy flour to the pp-composite material improved the retention of $L.$ $casei$ in the bioreactor, as did the addition of zein to pp-composite chips containing cellulose or oat hulls. Mixed culture performance was consistently higher on all supports compared to pure culture, even on supports made of polypropylene alone. The addition of soy flour to pp-composite chips generally enhanced the lactic acid production (see, TABLES 13-a,b).

Criteria for pp-composite support selection. The overall stability of fermentations for each of the different supports was evaluated by examining the mean value for the six different flow (dilution) rates (see, TABLES 13-a,b). The results showed a high lactic acid production, particularly at the faster flow rates, an increase in lactic acid production by doubling the flow rate, and an increase in lactic acid production in fermentation systems with pp-composite supports compared to a suspension culture at the corresponding flow rate (see, TABLE 12-a,b,c and FIGS. 2A and 2B). The results show that pp-composite chips containing oat hulls and zein had the best results in pure culture fermentations, and chips containing oat hull and soy flour had the best results for mixed culture fermentations.

Mixed culture biofilm cell immobilization prevented cell washout from the reactor system, and increased lactic acid production. Pure culture interaction by $L.$ $casei$ with the different plant-derived organic polymers resulted in cell immobilization and improved lactic acid production.

EXAMPLE 5

TREATMENT OF CONTAMINATED WATER

The present thermoplastic composite supports may be used in a system for treating water to process or degrade one or more contaminant substances, such as petrochemicals, herbicides and pesticides. Synthetic polymer composite supports can be prepared by combining the synthetic polymer with a desired plant-derived organic polymer, and forming the material into a desired size and shape of the support according to the design of the bioreactor. A specific microbial consortium capable of degrading the chemical contaminant of interest would then be allowed to attach to and grow on the supports. This can be achieved under a continuous fermentation system in the presence of a simple or complex medium. Biodegradation of the contaminant can be monitored by means of high pressure liquid chromatography (HPLC) or gas-liquid chromatography, depending on the contaminant compound. Once the mixed or pure culture has been immobilized on the supports the bioreactor is ready for use. The appropriate size and shape of the supports will depend on the final bioreactor design (i.e., long column versus short tank). In addition, aeration and pH are parameters to be controlled in the system. Continuous addition of nutritional factors such as nitrogen and vitamins can also be required. The size of the bioreactor will depend on the volume of water to be treated and the concentration of chemical contaminant to be bioremediated.

Advantageously, since the present polymer composite supports are lightweight and can float at the surface of the water, there are no special requirements with respect to the construction of the bioreactors to allow incorporation of the supports into the system.

The biofilm reactor chips can be shipped to the site of interest, for example, under refrigeration in liquid or freeze-dried. The biofilm reactor can then be placed on-line with the flow of water to treated.

The present biofilm reactors can take the place of activated carbon filters, producing as degradation products $CO_2$ and $H_2O$. The effluent of the bioreactor can be periodically monitored to insure complete degradation of the contaminant has occurred. Cell mass can occasionally become sloughed-off of the support, but can be replaced naturally with a fresh culture over time. If handled properly, the life of the biofilm reactor can be several years. Furthermore, by combining a support having an established and desired biofilm with a fresh, uninoculated support, the microorganisms from the established biofilm reactor will naturally inoculate the new supports.

EXAMPLE 6

TREATMENT OF INDUSTRIAL LAGOONS

Due to the lightweight nature of the present composite supports, floating aeration devices can be constructed for the treatment of industrial waste lagoons to reduce the biochemical oxygen demand. A biofilm reactor can be prepared in the laboratory or at a field site, by combining a suitable polymer composite support with a consortium of organisms that are capable of degrading contaminants, as for example, kraft pulp in a waste stream. Over a period of use, an aeration lagoon will naturally enrich for microorganisms which are able to degrade the compounds associated with a particular waste stream. Therefore, a consortium of these organisms can be naturally immobilized on these novel supports by simply passing the waste stream over the supports. If prepared in the laboratory, biofilm containing supports can be shipped, as for example, under refrigeration in water, or as a freeze-dried culture.

In a modified floating aeration system, the biofilm reactors can be contained in a float structure, and waste can be continually pumped from the lagoon and sprayed over the float containing the biofilm reactor in order to accelerate degradation. The biologically-treated water can then be returned to the lagoon through the bottom of the float structure. The advantage of using such a modified system is a higher oxygen tension, and the placement of compounds to be degraded in close proximity with the biocatalyts (i.e., the microorganisms) which can accelerate biodegradation.

Biofilm formation over additional supports can be achieved by using supports with established biofilms as a seed for new supports. This process will promote the introduction of additional floating biofilm reactors into the lagoon. Advantageously, because the units can float at the surface of the lagoons, no additional space would be required at the plant for this treatment.

TABLE 1

Formulation of Polypropylene Composite Supports.[a]

| PP-Composite chip | Plant-derived organic polymer (%) | Growth Enhancing Agent (minor amt.) |
|---|---|---|
| Polypropylene | — | — |
| Cellulose | 25 | — |
| Cellulose-Soy Flour | 20 | Soy Flour |
| Cellulose-Zein | 20 | Zein |
| Corn Fiber | 25 | — |
| Corn Fiber-Soy Flour | 20 | Soy Flour |
| Corn Fiber-Zein | 20 | Zein |
| Corn Starch | 25 | — |
| Corn Starch-Soy Flour | 20 | Soy Flour |
| Corn Starch-Zein | 20 | Zein |
| Oat Hulls | 25 | — |
| Oat Hulls-Soy Flour | 20 | Soy Flour |
| Oat Hulls-Zein | 20 | Zein |
| Soy Hulls | 25 | — |
| Soy Hulls-Soy Flour | 20 | Soy Flour |
| Soy Hulls-Zein | 20 | Zein |
| Carboxymethyl Cellulose | 25 | — |
| Soy Flour | 20 | — |
| Zein | 25 | — |
| Xylan | 25 | — |

[a]Seventy-five percent of each chip consisted of polypropylene.

TABLE 2

The potential biofilm forming bacteria, medium and incubation temperature used in the study.

| Microorganism | Medium[a] | Incubation temp (°C.) |
|---|---|---|
| *Bacillus licheniformis* (NRRL NRS 1264) | SSB | 30 |
| *Bacillus stearothermophilus* (NRRL B 1172) | SSB | 45 |
| *Lactobacillus amylophilus* (NRRL B 4437) | MRS | 25 |
| *Lactobacillus amylophilus* (NRRL B 4440) | MRS | 25 |
| *Lactobacillus casei* (ATCC 11443) | MRS | 37 |
| *Lactobacillus delbruekii* (mutant) | MRS | 45 |
| *Pseudomonas amyloderamosa* (ATCC 21262) | 3 | 30 |
| *Pseudomonas fragi* (ATCC 4973) | 3 | 25 |
| *Pseudomonas thermocarboxydovorans* (ATCC 35961) | 1492 | 45 |
| *Streptomyces badius* 252 (ATCC 39117) | 196 | 37 |
| *Streptomyces setonii* 75Vi2 (ATCC 39116) | 19 | 37 |
| *Streptomyces viridosporous* T7A (ATCC 39115) | 196 | 37 |
| *Thermomonospora curvata* (ATCC 19995) | 1489 | 45 |
| *Thermonospora fusca* (ATCC 27730) | 74 | 45 |
| *Thermoactinomyces vulgaris* (ATCC 43649) | 18 | 45 |

[a]Medium composition:
SSB: 10 g/l Soluble Starch, 5 g/l Yeast Extract in nitrogen free salt solution
MRS: 55 g/l Lactobacillus MRS Broth
Media 3: 3 g/l Beef Extract, 5 g/l Peptone
Media 18: 30 g/l Trypticase Soy Broth
Media 196: 6 g/l Yeast Extract in nitrogen-free salt solution
Media 741: 3 g/l Tryptone, 3 g/l Yeast Extract, 3 g/l Glucose, 1 g/l $K_2HPO_4$
Media 1489: 10 g/l Dextrin, 2 g/l Tryptone, 1 g/l Meat Extract, 1 g/l Yeast Extract, 2 mg/l $CoCl_2$
Media 1492: 2 g/l pyruvate and mineral solution.
All numbered medium are from the American Type Culture Collection catalogue of bacteria and bacriophages, 17th ed.

TABLE 3

Polypropylene composite supports formulation.[a]

| PP-Composite chip | Plant-Derived Organic Polymer (%) | Growth Enhancing Agent (5%) |
|---|---|---|
| Polypropylene | — | — |
| Carboxyl Methyl Cellulose | 25 | — |
| Cellulose | 25 | — |
| Cellulose-Soy Flour | 20 | Soy Flour |
| Cellulose-Zein | 20 | Zein |
| Oat Hulls | 25 | — |
| Oat Hulls-Soy Flour | 20 | Soy Flour |
| Oat Hulls-Zein | 20 | Zein |
| Soy Flour | 25 | — |
| Soy Hulls | 25 | — |
| Soy Hulls-Soy Flour | 20 | Soy Flour |
| Soy Hulls-Zein | 20 | Zein |
| Zein | 25 | — |
| Xylan | 25 | — |

[a]Seventy-five percent of each chip consisted of polypropylene.

TABLE 4

Summary of select biofilm-forming bacteria with best pp-composite support, and optimum incubation time for biofilm formation.

| Biofilm-forming Bacteria | Best Polyprop. Support | Biofilm Formation[a] | | |
|---|---|---|---|---|
| | | 4 days | 8 days | 15 days |
| *Pseudomonas fragi* | 20% oat hulls plus 5% zein | − | − | ++ |
| 0.8% nutrient broth at room temperature | 20% oat hulls plus 5% soy flour | − | − | ++ |
| *Streptomyces viridosporus* T7A | 20% soy hulls plus 5% zein | + | ++ | +++ |
| 0.6% yeast extract broth at 37° C. | 20% soy hulls plus 5% soy flour | + | ++ | ++ |
| *Thermoactinomyces vulgaris* | 25% oat hulls | + | ++ | ++ |
| 3% Trypticase Soy Broth at 45° C. | 20% oat hulls plus 5% zein | + | + | ++ |
| | 25% zein | + | + | +++ |

[a]color intensity after gram staining.

TABLE 5

Biofilm formation in batch fermentation on different solid supports in batch fermentation.

| Microorganisms | Solid Supports | | |
|---|---|---|---|
| | Porcelain Berl Saddles | Pea Gravels | 3M-Macrolite Shperes |
| *B. licheniformis* | − | nd | − |
| *B. stearothermophilus* | − | nd | − |
| *L. amylophilus* (NRRL B 4337) | − | nd | − |
| *L. amylophilus* (NRRL B 4440) | − | nd | − |
| *L. casei* | nd | nd | nd |
| *L. delbrueekii* (mutant) | − | nd | nd |
| *P. amyloderamosa* | − | nd | + |
| *P. aeruginosa* | − | nd | nd |
| *P. fluorescens* | − | nd | nd |
| *P. fragi* | nd | + | nd |
| *P. thermocarboxydovorans* | − | − | − |
| *S. badius* 252 | − | − | + |
| *S. setonii* 75Vi2 | − | + | + |
| *S. viridosporous* T7A | − | + | + |
| *T. curvata* | − | − | + |
| *T. fusca* | − | + | + |
| *T. vulgaris* | − | − | + |

[a]Minus (−) means no biofilm;
Plus (+) means biofilm present;
nd means not determined

TABLE 6

Effects of autoclaving porcelain berl saddles in complex medium on support dried weight.

| Medium | Medium composition (g/l) | Weight Gain (%) |
|---|---|---|
| Lactobacillus MRS Broth | 55 | 0.46 |
| Trypticase Soy Broth | 30 | 0.33 |
| Soluble Starch Broth | 15 | 0.25 |
| Yeast Extract Medium | 6 | 0.17 |
| Nutrient Broth | 8 | 0.13 |

TABLE 7

Acid-Base Treated Porcelain Berl Saddles

| Soaking Agent | Weight Gain (%) | | |
|---|---|---|---|
| | 5% Yeast Ext-Starch | 5% Yeast Extract | 5% Starch |
| 2N $H_2SO_4$ | −0.63 | −0.58 | −0.42 |
| 2N HCl | 0.88 | 0.40 | 0.46 |
| 2N NaOH | 0.01 | −0.52 | −0.07 |
| Water | 0.71 | 0.34 | 0.36 |

TABLE 8

Biofilm formation on pp-composite chips as determined by clumping after a 6 week continuous fermentation.[a]

| PP-Composite Chips | Biofilm Formation | | |
|---|---|---|---|
| | *P. fragi* | *S. viridosporus* T7A | *T. vulgaris* |
| Carboxyl Methyl Cellulose | nd | − | nd |
| Cellulose | − | + | + |
| Cellulose-Soy Flour | ++ | ++ | +++ |
| Cellulose-Zein | + | + | +++ |
| Oat Hulls | + | +++ | +++ |
| Oat Hulls-Soy Flour | ++ | +++ | + |
| Oat Hulls-Zein | ++ | + | +++ |
| Soy Flour | nd | nd | − |
| Soy Hulls | − | ++ | ++ |
| Soy Hulls-Soy Flour | + | +++ | + |
| Soy Hulls-Zein | + | ++ | + |
| Zein | + | + | +++ |
| Xylan | nd | − | nd |

[a]Strength of clumping (+); no biofilm formation (−); not determined (nd).

TABLE 9

Continuous fermentation of pure and mixed-culture lactic acid fermentations with *Pseudomonas fragi* and *Lactobacillus acidophilus*[a]

| | Pure Culture | | | Mixed Culture | | |
|---|---|---|---|---|---|---|
| Flow Rate (ml/min) | Optical Density (620 nm) | Lactic Acid (g/l) | Percent Yield | Optical Density (620 nm) | Lactic Acid (g/l) | Percent Yield |
| Oat Hulls-Soy Flour | | | | | | |
| 0.06 | 1.02 | 2.28 | 67.45 | 0.06 | 2.56 | 90.70 |
| 0.12 | 0.70 | 2.46 | 70.50 | 0.45 | 2.25 | 84.30 |
| 0.24 | 0.75 | 2.36 | 81.95 | 0.32 | 2.49 | 100.00 |
| 0.48 | 0.60 | 3.97 | 100.00 | 0.22 | 2.59 | 66.20 |
| 0.96 | 0.44 | 1.66 | 74.47 | nd | nd | nd |
| 1.92 | 0.36 | 0.56 | 100.00 | nd | nd | nd |
| Oat Hull-Zein | | | | | | |
| 0.06 | 0.32 | 1.06 | 50.96 | 1.62 | 2.92 | 25.15 |
| 0.12 | 0.28 | 1.21 | 91.60 | 1.10 | 4.15 | 61.03 |
| 0.24 | 0.38 | 2.13 | 89.87 | 2.16 | 4.82 | 80.00 |
| 0.48 | 0.32 | 2.10 | 83.30 | 0.58 | 3.59 | 81.00 |
| 0.96 | 0.52 | 1.91 | 84.50 | 0.56 | 2.95 | 85.75 |
| 1.92 | 0.22 | 0.98 | 59.00 | nd | nd | nd |

[a]Pure culture studies were with *L. acidophilus* alone and mixed culture were with *P. fragi* and *L. acidophilus*. All values were taken at steady state (24 hour culture) and percent yield was calculated by dividing produced lactic acid by consumed glucose times 100%.

TABLE 10

Continuous fermentation of pure and mixed-culture lactic acid fermentations with *Streptomyces viridosporus* T7A and *Lactobacillus casei*[a]

| | Pure Culture | | | Mixed Culture | | |
|---|---|---|---|---|---|---|
| Flow Rate (ml/min) | Optical Density (620 nm) | Lactic Acid (g/l) | Percent Yield | Optical Density (620 nm) | Lactic Acid (g/l) | Percent Yield |
| Soy Hulls-Zein | | | | | | |
| 0.06 | 0.36 | 9.98 | 100.00 | 0.60 | 8.80 | 60.65 |
| 0.12 | 0.44 | 9.83 | 92.04 | 0.68 | 13.00 | 86.66 |
| 0.24 | 1.44 | 10.17 | 100.00 | 0.70 | 12.57 | 96.91 |
| 0.48 | 1.44 | 8.98 | 100.00 | 0.90 | 10.28 | 100.00 |
| 0.96 | 1.56 | 7.12 | 100.00 | 1.50 | 8.04 | 96.66 |
| 1.92 | nd | nd | nd | 0.80 | 4.40 | 100.00 |
| Soy Hull-Soy Flour | | | | | | |
| 0.06 | 0.72 | 9.27 | 84.90 | 0.52 | 9.61 | 64.06 |
| 0.12 | 3.48 | 9.64 | 64.30 | 1.26 | 11.84 | 78.94 |
| 0.24 | 1.98 | 10.25 | 82.10 | 0.78 | 12.13 | 97.27 |
| 0.48 | 2.04 | 9.31 | 100.00 | 1.08 | 10.43 | 100.00 |
| 0.96 | 1.50 | 6.83 | 95.12 | 1.68 | 8.73 | 100.00 |
| 1.92 | 1.00 | 4.91 | 100.00 | 1.1 | 5.97 | 100.00 |

[a]Pure culture studies were with *L. acidophilus* alone and mixed culture were with *P. fragi* and *L. acidophilus*. All values were taken at steady state (24 hour culture) and percent yield was calculated by dividing produced lactic acid by consumed glucose times 100%.

TABLE 11

Continuous fermentation of pure and mixed-culture lactic acid fermentations with *Thermoactinomyces vulgaris* and *Lactobacillus delbrueckii*[a]

| | Pure Culture | | | Mixed Culture | | |
|---|---|---|---|---|---|---|
| Flow Rate (ml/min) | Optical Density (620 nm) | Lactic Acid (g/l) | Percent Yield | Optical Density (620 nm) | Lactic Acid (g/l) | Percent Yield |
| Oat Hull | | | | | | |
| 0.06 | 0.54 | 0.82 | 16.40 | 1.80 | 5.10 | 50.00 |
| 0.12 | 0.58 | nd | nd | 1.08 | 4.59 | 67.80 |
| 0.24 | 0.58 | 2.90 | 51.97 | 0.34 | 2.78 | 81.00 |
| 0.48 | 0.44 | 3.33 | 58.60 | 0.33 | 2.14 | 80.00 |
| 0.96 | 0.52 | 3.17 | 64.17 | 0.21 | 1.34 | 65.68 |
| 1.92 | 0.51 | 1.85 | 49.50 | 0.17 | 1.03 | 97.10 |
| Oat Hull-Zein | | | | | | |
| 0.06 | 0.19 | 1.74 | 65.40 | 0.96 | 5.52 | 41.00 |
| 0.12 | 0.19 | 5.19 | 88.20 | 0.56 | 3.60 | 60.30 |
| 0.24 | 0.22 | 1.69 | 97.60 | 0.22 | 3.92 | 82.50 |
| 0.48 | 0.28 | 1.67 | 86.00 | 0.45 | 2.33 | 70.00 |
| 0.96 | 0.24 | 1.05 | 49.50 | 0.23 | 1.95 | 76.47 |
| 1.92 | nd | nd | nd | nd | nd | nd |
| Zein | | | | | | |
| 0.06 | 0.14 | 1.30 | 87.20 | 0.84 | nd | nd |
| 0.12 | 0.10 | 0.86 | 68.20 | 0.26 | 4.09 | 46.69 |
| 0.24 | 0.07 | 2.20 | 100.00 | 1.02 | 4.42 | 89.29 |
| 0.48 | 0.12 | 1.23 | 85.40 | 0.42 | 2.77 | 78.60 |
| 0.96 | 0.12 | 1.45 | 91.19 | 0.32 | 2.18 | 95.20 |
| 1.92 | 0.06 | 2.03 | 100.00 | 0.25 | 2.21 | 100.00 |

[a]Pure culture studies were with *L. acidophilus* alone and mixed culture were with *P. fragi* and *L. acidophilus*. All values were taken at steady state (24 hour culture) and percent yield was calculated by dividing produced lactic acid by consumed glucose times 100%.

TABLE 12a

Percent yield and productivity for lactic acid production by L. casie in pure and mixed culture continuous fermentation with different pp-composite chips.[a]

| Flow Rate (ml/min) | Pure Yield | Pure Prod | Mixed Yield | Mixed Prod | Pure Yield | Pure Prod | Mixed Yield | Mixed Prod | Pure Yield | Pure Prod | Mixed Yield | Mixed Prod |
|---|---|---|---|---|---|---|---|---|---|---|---|---|
| | Cellulose | | | | Cellulose - Soy Flour | | | | Cellulose - Zein | | | |
| 0.06 | 81.7 | 0.04 | 53.3 | 0.04 | 76.9 | 0.05 | 61.6 | 0.04 | 80.6 | 0.04 | 44.2 | 0.03 |
| 0.12 | 100 | 0.07 | 72.9 | 0.09 | 85.5 | 0.08 | 63.3 | 0.09 | 84.9 | 0.07 | 42.7 | 0.06 |
| 0.24 | 100 | 0.12 | 78.0 | 0.18 | 93.1 | 0.12 | 75.1 | 0.19 | 87.6 | 0.12 | 64.6 | 0.15 |
| 0.48 | 70.5 | 0.15 | 72.4 | 0.29 | 75.4 | 0.19 | 73.1 | 0.31 | 78.0 | 0.22 | 58.9 | 0.19 |
| 0.96 | 68.8 | 0.22 | 68.2 | 0.44 | 73.1 | 0.38 | 67.3 | 0.48 | 70.0 | 0.35 | 61.8 | 0.30 |
| 1.92 | 61.0 | 0.38 | 68.2 | 0.68 | 76.2 | 0.81 | 66.1 | 0.75 | 69.0 | 0.59 | 73.7 | 0.46 |
| | Corn Hulls | | | | Corn Hulls - Soy Flour | | | | Corn Hulls - Zein | | | |
| 0.06 | 81.5 | 0.04 | 45.9 | 0.03 | 61.3 | 0.04 | 59.5 | 0.04 | 82.2 | 0.03 | 53.2 | 0.03 |
| 0.12 | 81.3 | 0.04 | 54.5 | 0.08 | 77.6 | 0.04 | 68.5 | 0.09 | 86.8 | 0.04 | 58.6 | 0.08 |
| 0.24 | 84.9 | 0.07 | 70.0 | 0.19 | 81.0 | 0.08 | 75.2 | 0.19 | 97.0 | 0.07 | 67.0 | 0.17 |
| 0.48 | 89.3 | 0.14 | 78.7 | 0.33 | 85.9 | 0.14 | 86.4 | 0.32 | 91.1 | 0.15 | 75.6 | 0.33 |
| 0.96 | 93.5 | 0.26 | 86.4 | 0.50 | 86.9 | 0.19 | 89.2 | 0.50 | 93.0 | 0.25 | 83.1 | 0.52 |
| 1.92 | 100 | 0.43 | 84.3 | 0.76 | 50.0 | 0.31 | 100 | 0.82 | nd | nd | nd | nd |

[a]Yield (%) was calculated by produced lactic acid (g/l) divided by consumed glucose (g/l) 100%.
Productivity (g/l) was calculated by lactic acid per hour calculated as produced lactic acid (g/l) times flow rate (1/hr).
ND is for not determined.

TABLE 12b

| Flow Rate (ml/min) | Pure Yield | Pure Prod | Mixed Yield | Mixed Prod | Pure Yield | Pure Prod | Mixed Yield | Mixed Prod | Pure Yield | Pure Prod | Mixed Yield | Mixed Prod |
|---|---|---|---|---|---|---|---|---|---|---|---|---|
| | Corn Starch | | | | Corn Starch - Soy Flour | | | | Corn Starch - Zein | | | |
| 0.06 | 100 | 0.03 | 60.1 | 0.04 | 85.9 | 0.04 | 50.0 | 0.04 | 83.0 | 0.04 | 67.6 | 0.05 |
| 0.12 | 100 | 0.03 | 69.0 | 0.08 | 91.3 | 0.03 | 100 | 0.08 | 91.5 | 0.07 | 72.5 | 0.103 |
| 0.24 | 92.7 | 0.06 | 77.4 | 0.15 | 90.2 | 0.06 | 67.7 | 0.14 | 94.0 | 0.13 | 85.5 | 0.18 |
| 0.48 | 100 | 0.12 | 88.1 | 0.28 | 98.3 | 0.13 | 79.6 | 0.27 | 76.1 | 0.24 | 74.3 | 0.30 |
| 0.96 | 100 | 0.19 | 69.4 | 0.38 | 94.7 | 0.25 | 86.5 | 0.49 | 72.2 | 0.33 | 64.4 | 0.32 |
| 1.92 | 100 | 0.26 | 100 | 0.87 | 100 | 0.39 | 88.0 | 1.04 | 68.2 | 0.56 | 66.8 | 0.61 |
| | Oat Hulls | | | | Oat Hulls - Soy Flour | | | | Oat Hulls - Zein | | | |
| 0.06 | 77.1 | 0.03 | 54.1 | 0.03 | 62.6 | 0.03 | 69.1 | 0.04 | 73.8 | 0.04 | 56.2 | 0.04 |
| 0.12 | 71.4 | 0.05 | 42.9 | 0.06 | 60.4 | 0.06 | 59.5 | 0.08 | 85.7 | 0.05 | 59.5 | 0.08 |
| 0.24 | 84.4 | 0.11 | 64.2 | 0.14 | 76.6 | 0.13 | 67.6 | 0.18 | 89.5 | 0.15 | 74.3 | 0.17 |
| 0.48 | 94.2 | 0.24 | 71.4 | 0.29 | 100 | 0.24 | 81.7 | 0.35 | 100 | 0.29 | 80.7 | 0.29 |
| 0.96 | 93.5 | 0.40 | 82.1 | 0.50 | 100 | 0.52 | 82.7 | 0.60 | 97.0 | 0.41 | 89.0 | 0.51 |
| 1.92 | 90.6 | 0.64 | 76.8 | 0.81 | 96.5 | 0.72 | 83.1 | 0.93 | 100 | 0.69 | 75.1 | 0.68 |

[a]Yield (%) was calculated by produced lactic acid (g/l) divided by consumed glucose (g/l) 100%.
Productivity (g/l) was calculated by lactic acid per hour calculated as produced lactic acid (g/l) times flow rate (1/hr).
ND is for not determined.

TABLE 12c

| Flow Rate (ml/min) | Pure Yield | Pure Prod | Mixed Yield | Mixed Prod | Pure Yield | Pure Prod | Mixed Yield | Mixed Prod | Pure Yield | Pure Prod | Mixed Yield | Mixed Prod |
|---|---|---|---|---|---|---|---|---|---|---|---|---|
| | Soy Hulls | | | | Soy Hulls - Soy Flour | | | | Soy Hulls - Zein | | | |
| 0.06 | 77.9 | 0.03 | 58.6 | 0.04 | 83.9 | 0.04 | 63.0 | 0.04 | 78.4 | 0.03 | 69.1 | 0.04 |
| 0.12 | 69.6 | 0.06 | 61.7 | 0.09 | 88.9 | 0.07 | 67.9 | 0.08 | 77.1 | 0.06 | 60.6 | 0.09 |
| 0.24 | 83.5 | 0.11 | 73.3 | 0.19 | 98.6 | 0.14 | 87.5 | 0.22 | 85.5 | 0.11 | 71.4 | 0.16 |
| 0.48 | 88.3 | 0.27 | 83.5 | 0.33 | 90.6 | 0.27 | 75.8 | 0.28 | 97.8 | 0.24 | 100 | 0.31 |
| 0.96 | 90.5 | 0.51 | 87.2 | 0.59 | 73.6 | 0.39 | 100 | 0.54 | 95.8 | 0.48 | 88.9 | 0.54 |

TABLE 12c-continued

| | | | | | | | | | | | |
|---|---|---|---|---|---|---|---|---|---|---|---|
| 1.92 | 93.6 | 0.80 | 89.5 | 0.88 | 69.9 | 0.60 | 68.3 | 0.58 | 100 | 0.72 | 95.2 | 0.71 |

| | Control | | Polypropylene | | | |
|---|---|---|---|---|---|---|
| | Pure | | Pure | | Mixed | |
| Flow Rate (ml/min) | Yield | Prod | Yield | Prod | Yield | Prod |
| 0.06 | 78.3 | 0.03 | 100 | 0.02 | 62.2 | 0.04 |
| 0.12 | 86.0 | 0.05 | 85.0 | 0.04 | 67.8 | 0.09 |
| 0.24 | 86.8 | 0.07 | 96.1 | 0.09 | 83.4 | 0.17 |
| 0.48 | 100 | 0.06 | 96.1 | 0.18 | 90.1 | 0.25 |
| 0.96 | 100 | 0.12 | 100 | 0.20 | 82.6 | 0.38 |
| 1.92 | 100 | 0.22 | 90.8 | 0.33 | 86.1 | 0.47 |

[a]Yield (%) was calculated by produced lactic acid (g/l) divided by consumed glucose (g/l) 100%.
Productivity (g/l) was calculated by lactic acid per hour calculated as produced lactic acid (g/l) times flow rate (1/hr).
ND is for not determined.

TABLE 13a

Average values of six different flow rates on various pp-composite supports.[a]
PURE CULTURE

| SUPPORTS | L.A. | Yld | Pro | Doub | Comp |
|---|---|---|---|---|---|
| Control | 4.50 | 91.9 | 0.09 | 1.51 | 1.00 |
| Polypropylene | 5.21 | 97.5 | 0.14 | 1.75 | 1.49 |
| Cellulose | 6.87 | 80.3 | 0.16 | 1.58 | 1.70 |
| Cellulose-Soy Flour | 8.68 | 80.0 | 0.27 | 1.79 | 2.44 |
| Cellulose- Zein | 8.02 | 78.4 | 0.23 | 1.71 | 2.25 |
| Corn Fiber | 9.50 | 88.4 | 0.16 | 1.67 | 1.56 |
| Corn Fiber-Soy Flour | 9.08 | 73.8 | 0.13 | 1.54 | 1.39 |
| Corn Fiber-Zein | 7.94 | 75.0 | 0.09 | 1.35 | 1.19 |
| Corn Starch | 7.38 | 98.8 | 0.12 | 1.61 | 1.17 |
| Corn Starch-Soy Flour | 9.08 | 73.8 | 0.13 | 1.54 | 1.39 |
| Corn Starch-Zein | 8.08 | 80.8 | 0.23 | 1.71 | 2.27 |
| Oat Hulls | 7.55 | 85.2 | 0.25 | 1.81 | 2.30 |
| Oat Hulls-Soy Flour | 8.43 | 82.7 | 0.28 | 1.87 | 2.61 |
| Oat Hulls-Zein | 8.53 | 91.0 | 0.27 | 1.86 | 2.58 |
| Soy Hulls | 8.22 | 83.9 | 0.30 | 1.93 | 2.65 |
| Soy Hulls-Soy Flour | 8.60 | 84.3 | 0.25 | 1.76 | 2.50 |
| Soy Hulls-Zein | 7.86 | 89.1 | 0.27 | 1.88 | 2.48 |
| Criteria limits (≧) | 8.00 | 90.0 | 0.25 | 1.8 | 2.50 |

[a]Each value is the mean (average) stated for the different flow rates at steady state.
L.A. = lactic acid concentration (g/l)
Yld = yield, or percent conversion of glucose into lactic acid.
Pro = productivity, or grams of lactic acid produced per hour.
Doub = doubling, or the increase in productivity at a specific flow rate compared to preceding flow rate.
Comp = comparison, or the ratio of productivity compared to the productivity of the control at the same flow rate.

TABLE 13b

Average values of six different flow rates on various pp-composite supports.[a]
MIXED CULTURE

| SUPPORTS | L.A. | Yld | Pro | Doub | Comp |
|---|---|---|---|---|---|
| Polypropylene | 9.21 | 78.7 | 0.23 | 1.63 | 2.47 |
| Cellulose | 9.90 | 68.8 | 0.29 | 1.81 | 2.83 |
| Cellulose-Soy Flour | 10.48 | 67.8 | 0.31 | 1.79 | 3.03 |
| Cellulose- Zein | 7.09 | 57.7 | 0.20 | 1.77 | 1.96 |
| Corn Fiber | 9.68 | 69.9 | 0.31 | 2.05 | 3.00 |
| Corn Fiber-Soy Flour | 10.81 | 79.8 | 0.33 | 1.82 | 3.16 |
| Corn Fiber-Zein | 8.71 | 56.3 | 0.19 | 1.68 | 2.44 |
| Corn Starch | 9.27 | 77.3 | 0.30 | 1.91 | 2.74 |
| Corn Starch-Soy Flour | 10.81 | 79.8 | 0.33 | 1.82 | 3.16 |
| Corn Starch-Zein | 10.04 | 71.9 | 0.26 | 1.70 | 2.69 |
| Oat Hulls | 8.89 | 65.2 | 0.30 | 1.89 | 2.79 |
| Oat Hulls-Soy Flour | 11.17 | 74.0 | 0.37 | 1.86 | 3.42 |
| Oat Hulls-Zein | 9.66 | 72.5 | 0.29 | 1.80 | 2.85 |

TABLE 13b-continued

Average values of six different flow rates on various pp-composite supports.[a]
MIXED CULTURE

| SUPPORTS | L.A. | Yld | Pro | Doub | Comp |
|---|---|---|---|---|---|
| Soy Hulls | 10.99 | 75.6 | 0.35 | 1.85 | 3.32 |
| Soy Hulls-Soy Flour | 10.45 | 77.1 | 0.29 | 1.79 | 2.96 |
| Soy Hulls-Zein | 10.18 | 81.3 | 0.31 | 1.78 | 3.01 |
| Criteria limits (≧) | 10.0 | 80.0 | 0.30 | 1.9 | 3.0 |

[a]Each value is the mean (average) stated for the different flow rates at steady state.
L.A. = lactic acid concentration (g/l)
Yld = yield, or percent conversion of glucose into lactic acid.
Pro = productivity, or grams of lactic acid produced per hour.
Doub = doubling, or the increase in productivity at a specific flow rate compared to preceding flow rate.
Comp = comparison, or the ratio of productivity compared to the productivity of the control at the same flow rate.

What is claimed is:

1. A biofilm reactor, comprising:
   (a) a solid support for immobilizing cells of a film-forming microorganism, the support being comprised of about 50–95 wt-% of a polyolefin synthetic polymer in admixture with about 5–50 wt-% of an organic polymeric plant material, which solid support is capable of remaining essentially intact for about 1–3 years in aqueous media; and
   (b) a film of a population of cells of the microorganism attached to a substantial proportion of the surface of the solid cell support.

2. The reactor according to claim 1, wherein the amount of the synthetic polymer is about 65–85 wt-%.

3. The reactor according to claim 1, wherein the polyolefin comprises polyethylene, polypropylene, polybutene, polyisoprene, polystyrene, polypentene, polymethylpentene, polybutadiene, polychloroprene, polyvinylchloride, polyvinylidene chloride, polyacrylonitrile, polyvinylacetate, polyacrylamide, or a copolymer thereof.

4. The reactor according to claim 1, wherein the polyolefin comprises polyethylene or polypropylene.

5. The reactor according to claim 1, wherein the organic polymeric plant material comprises stovers, corn hulls, oat hulls, soy hulls, milkweed pods, leaves, seeds, fruit, grass, wood, paper, algae, cotton, hemp, flax, jute, ramie, kapok, or any combination thereof.

6. The reactor according to claim 1, wherein the organic polymeric plant material comprises corn starch, potato starch, wheat starch, rice starch, waxy rice starch, tapioca starch, oat starch, rye starch, barley starch, sorghum starch, mung bean starch, sweet potato starch, or any combination thereof.

7. The reactor according to claim 1, wherein the organic polymeric plant material comprises zein, xylan, gluten, soybean protein, hordein, kafirin, avenin, or any combination thereof.

8. The reactor according to claim 1, wherein the organic polymeric plant material comprises a modified cellulose selected from the group consisting of methylcellulose, carboxymethylcellulose, hydroxyalkyl cellulose, cellulose acetate, nitrocellulose, rayon, cellophane, viscose, and any combination thereof.

9. The biofilm reactor according to claim 1, wherein the microorganism comprises a film-forming organism selected from the group consisting of Pseudomonas, Streptomyces, Thermoactinomyces, Aspergillus, Rhizopus, Penicillium, and Saccharomyces.

10. The biofilm reactor according to claim 1, further comprising:
  (c) a population of cells of a second microorganism attached to the cells of the film-forming organism of step (b).

11. The biofilm reactor according to claim 10, wherein the second microorganism is capable of substantially fermenting a carbohydrate to a single organic acid or organic alcohol.

12. The biofilm reactor according to claim 10, wherein the second microorganism is selected from the group consisting of Lactobacillus, Zymononas, Clostridium, Acetobacterium, Propionibacterium and Acetogenium.

13. The reactor of claim 1, wherein the support further comprises a microbial growth-enhancing amount of an animal-derived growth-enhancing agent selected from the group consisting of casein, albumin, collagen, gelatin, keratin and a mixture thereof.

14. The reactor of claim 1, wherein the support comprises a plasticizer in an amount effective to facilitate processing of said support.

15. The reactor of claim 1, wherein the support comprises a lubricant in an amount effective to aid in the removal of said support from a dye or a mold.

16. A method of immobilizing cells of a microorganism on a solid support to form a biofilm reactor, comprising:
  (a) providing a solid support for immobilizing cells of a film-forming microorganism, the support being comprised of about 50–95 wt-% of a poyolefin synthetic polymer in admixture with about 5–50 wt-% of an organic polymeric plant material, which solid support is capable of remaining essentially intact for about 1–3 years in aqueous media; and
  (b) contacting the support with an amount of a live culture of film-forming microorganism cells for a time period effective for cells of the microorganism to attach to the surface of the support and form a film of microorganism cells on a substantial proportion of the surface of the support.

17. A method of producing a fermentation product within a biofilm reactor, comprising the steps of:
  (a) providing a solid support comprised of 50–95 wt-% of a polyolefin synthetic polymer in admixture with about 5–50 wt-% of an organic polymeric plant material, which solid support is capable of remaining essentially intact for about 1–3 years in aqueous media, the surface of the support having cells of a film-forming microorganism attached as a film over a substantial proportion of the surface of the support to form a biofilm reactor;
  (b) placing the biofilm reactor in a liquid medium comprising a substance to be fermented by the microorganism; and
  (c) allowing the microorganism to substantially ferment the substance to produce the fermentation product.

18. The method of claim 17, wherein the fermentation product comprises lactic acid, acetic acid, citric acid, succinic acid, propionic acid, ethanol, or butanol-acetone.

19. The method of claim 17, further comprising selecting a pH, temperature and dilution rate effective to produce the fermentation product at an amount of about 5 to 90 g/l per hour.

20. A method for treating water comprising a contaminant substance with a biofilm reactor, comprising:
  (a) providing a solid support comprised of about 50–95 wt-% of a polyolefin synthetic polymer in admixture with about 5–50 wt-% of an organic polymeric plant material, which solid support is capable of remaining essentially intact for about 1–3 years in aqueous media, the surface of the support having cells of a film-forming microorganism attached as a film over a substantial proportion of the surface of the support to form a biofilm reactor;
  (b) placing the biofilm reactor in the water comprising the contaminant substance to be metabolized by the microorganism; and
  (c) allowing the microorganism to substantially metabolize the contaminant substance.

* * * * *